(12) United States Patent
Norton et al.

(10) Patent No.: US 7,049,115 B2
(45) Date of Patent: May 23, 2006

(54) GENES ENCODING DENITRIFICATION ENZYMES

(75) Inventors: Kelley C. Norton, Avondale, PA (US); J. Martin Odom, Kennett Square, PA (US); Andreas J. Schenzle, Uhl Dinden (DE); Rick W. Ye, Hockessin, DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 307 days.

(21) Appl. No.: 09/789,161

(22) Filed: Feb. 20, 2001

(65) Prior Publication Data

US 2005/0084945 A1 Apr. 21, 2005

Related U.S. Application Data

(60) Provisional application No. 60/185,621, filed on Feb. 29, 2000.

(51) Int. Cl.
| | |
|---|---|
| C12N 9/06 | (2006.01) |
| C12N 1/20 | (2006.01) |
| C12N 1/14 | (2006.01) |
| C12N 15/00 | (2006.01) |
| C07H 21/04 | (2006.01) |

(52) U.S. Cl. .................. 435/191; 435/183; 435/189; 435/252.3; 435/254.2; 435/320.1; 536/23.2

(58) Field of Classification Search .............. 435/183, 435/189, 252.3, 254.2, 320.1; 536/23.2
See application file for complete search history.

(56) References Cited

PUBLICATIONS

Palmedo et al. Accession Z50198. Oct. 12, 1995.*
Palmedo et al. Resolution of the nirD locus for herne d1 synthesis of cytochrome cd1 (respiratory nitrite reductase) from *Pseudomonas stutzeri*. Eur J Biochem Sep. 15, 1995; 232(3):737–46.*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Kawasaki et al. Accession D50473. Feb. 1, 2000.*
Palmedo et al. Accession Q52521. Nov. 1, 1997.*
Palmedo et al. Resolution of the nirD locus for herne d–1 synthesis of cytochrome cd–1 (respiratory nitrite reductase) from *Pseudomonas stutzeri*, European Journal Biochemistry, vol. 232, No. 3, 1995; pp. 737–746, XP002208754.
Bedmar, *Bradythizobium japonicum* norCBQD gene cluster, Database Accession No. AJ132911, XP002208762.
Murai, K. et al., Cloning and nucleotide sequences of the nitric oxide reductase locus in *Paraoccus denitrificans* IFO 12442, Accession No. AB014090 XP002208763.
Ye et al., Appl. Environ. Microbiol. 60:1053–1058 (1994).
Zumft et al., Microbiol. Mol. Biol. Rev. 61:533–616 (1997).
Gottschalk, G., Bacterial Metabolism, p122–126 Springer–Verlag (1985).
Zumft, W. G., The Denitrifying Prokaryotes, The Prokaryotes vol. 1, p554–582 Springer–Verlag (1992).
Meteju et al., Enzyme Microb. Technol. 14: 172–183 (1992).
de Boer et al., Eur. J. Biochem. 242–592–600 (1996).
Palmedo et al., Eur. J. Biochem. 232 (3), 737–746 (1995).
Kawasaki et al., J. Bacteriol. 179(1), 235–242 (1997).
Lin et al., J. Bacteriol. 175:2370–2378 (1993).
Zumft et al., Eur. J. Biochem. 219:481–490 (1994).
Glockner et al., Biochem. Biophys. Acta 1277 (1–2) 6–12 (1996).
Cramm et al., J. Bacteriol 179(21), 6769–6777 (1997).
Hanson and Hanson, The Methanotrophic Bacteria Microbiol. Rev. 60: 439–471 (1996).
Lidstrom, L. E., The aerobic methylotrophic bacteria. The Prokaryotes, Springer–Verlag, p431–445 (1992).
Amaral, J. A., Archambault, S. R. Knowles, R., FEMS Microbiol Ecoli. 18: 289–298 (1995).
Ren, Tie, Roy, R., Knowles, R., Appl. Env. Microbiol. 66:9 3891–3897 (2000).
Yoshinari, T., Can J. Microbiol. 31 139–144 (1985).
Kramer, M., Baumgartner, M., Bender, M., Conrad, R., FEMS Microbiol. Lett. 345–350 (1990).

* cited by examiner

*Primary Examiner*—Manjunath N. Rao
*Assistant Examiner*—Christian L. Fronda

(57) ABSTRACT

This invention relates to the isolation of nucleic acid fragments from Methylamons sp. that encode enzymes involved in denitrification. The enzymes arc useful in denitrification reactions and for the identification of other denitrifying bacteria. In addition, this invention also relates to the construction of chimeric genes encoding all or a substantial portion of the present genes in sense or antisense orientation, wherein the expression of the chimeric genes results in production of altered levels of the present gene products in the recombinant host.

6 Claims, 3 Drawing Sheets

SEQUENCE LISTING

<160> NUMBER OF SEQ ID NOS: 22

<210> SEQ ID NO 1
<211> LENGTH: 1170
<212> TYPE: DNA
<213> ORGANISM: Methylomonas 16a
<220> FEATURE:
<223> OTHER INFORMATION: ORF1
<220> FEATURE:
<223> OTHER INFORMATION: nirF gene

<400> SEQUENCE: 1

| | | | | | |
|---|---|---|---|---|---|
| atgaagcgat | ttttaacgtt | ggcaggtgcg | gcttattttt | ttgccgcatc | ggctgttgca | 60 |
| gacctgcgcg | ccaccggcga | tttgggtgtc | gtgatcgagc | gcgagaccgg | cagtgtgcaa | 120 |
| gtcatcaaca | ccagcacgcc | caagatgctg | agccgcatcg | aaggcctggg | cgatttgtct | 180 |
| cacgcttcgg | tggtgttctc | gcgtgatcag | cgctatgcct | atgtattcgg | tcgcgacggc | 240 |
| ggcttgagca | aaatcgatct | gttgcaggac | aaaatcgaaa | acgcgtcgt | gcaagccggt | 300 |
| aacagcatag | gcggggcgat | ttcccaggat | ggcaaagtca | tcgccgtatc | caactatacg | 360 |
| ccgggcggcg | tcaagctgtt | cgatgccgag | accttggagc | agttggccga | gattccggcc | 420 |
| gtttacggcg | acgacaacca | gttatccaaa | gtggtcggct | tggtcgatgc | accgggcggt | 480 |
| cgtttcgttt | gcagcctgtt | cgaaggtaac | gagatttggc | tgatagacgc | caagaatcca | 540 |
| cgccagccgg | tcgtcaagaa | attcaaggac | atcggcaagc | ggcttatga | tgccttgctg | 600 |
| acgccggatg | ccatttctcta | cgcggccgga | ctgttcggcg | aaaaaggcct | ggctttgctg | 660 |
| gatttatggc | agccggagct | aggcgtcaaa | cacatcctgg | aagactacgg | caaggacgac | 720 |
| gagcaattgc | cggtttacaa | aatgccgcat | ctggaaggct | ggacggtagc | cggtgatctg | 780 |
| ctgttcgtgc | cggccatcgg | cctgcatgag | gtgttggtga | tcgataaaca | cgattgggag | 840 |
| ctggtcaaac | gcattccggt | cgtcggacaa | cccgtgttcg | tgatgtcccg | accggatggt | 900 |
| cgccaggtgt | gggtgaattt | cgccttccg | gacaatcaaa | ccgtacaggt | catagacgtc | 960 |
| aaggatttca | atatcgtcaa | gaccctgcaa | ccgggtaagg | ccgtgctgca | catggagttc | 1020 |
| agcccgcgcg | gcgaagccgt | ctggatggcg | gtgcgcgacg | aggacagggt | aatggtttac | 1080 |
| gacacggaca | gtttcaacga | aaccgcccgt | ctaccggcgc | aaaagcccag | cggcatcttt | 1140 |
| ttcagtaatc | gcgccaatca | gttggggctg | | | | 1170 |

<210> SEQ ID NO 2
<211> LENGTH: 390
<212> TYPE: PRT
<213> ORGANISM: Methylomonas 16a
<220> FEATURE:
<223> OTHER INFORMATION: NirF

<400> SEQUENCE: 2

Met Lys Arg Phe Leu Thr Leu Ala Gly Ala Ala Tyr Phe Phe Ala Ala
 1               5                  10                  15

Ser Ala Val Ala Asp Leu Arg Ala Thr Gly Asp Leu Gly Val Val Ile
                20                  25                  30

Glu Arg Glu Thr Gly Ser Val Gln Val Ile Asn Thr Ser Thr Pro Lys
            35                  40                  45

Met Leu Ser Arg Ile Glu Gly Leu Gly Asp Leu Ser His Ala Ser Val
        50                  55                  60

Val Phe Ser Arg Asp Gln Arg Tyr Ala Tyr Val Phe Gly Arg Asp Gly

```
                65                  70                  75                  80
Gly Leu Ser Lys Ile Asp Leu Leu Gln Asp Lys Ile Glu Lys Arg Val
                    85                  90                  95
Val Gln Ala Gly Asn Ser Ile Gly Gly Ala Ile Ser Gln Asp Gly Lys
            100                 105                 110
Val Ile Ala Val Ser Asn Tyr Thr Pro Gly Gly Val Lys Leu Phe Asp
            115                 120                 125
Ala Glu Thr Leu Glu Gln Leu Ala Glu Ile Pro Ala Val Tyr Gly Asp
        130                 135                 140
Asp Asn Gln Leu Ser Lys Val Gly Leu Val Asp Ala Pro Gly Gly
145                 150                 155                 160
Arg Phe Val Cys Ser Leu Phe Glu Gly Asn Glu Ile Trp Leu Ile Asp
                165                 170                 175
Ala Lys Asn Pro Arg Gln Pro Val Val Lys Phe Lys Asp Ile Gly
            180                 185                 190
Lys Arg Pro Tyr Asp Ala Leu Leu Thr Pro Asp Gly His Phe Tyr Ala
        195                 200                 205
Ala Gly Leu Phe Gly Glu Lys Gly Leu Ala Leu Leu Asp Leu Trp Gln
        210                 215                 220
Pro Glu Leu Gly Val Lys His Ile Leu Glu Asp Tyr Gly Lys Asp Asp
225                 230                 235                 240
Glu Gln Leu Pro Val Tyr Lys Met Pro His Leu Glu Gly Trp Thr Val
                245                 250                 255
Ala Gly Asp Leu Leu Phe Val Pro Ala Ile Gly Leu His Glu Val Leu
            260                 265                 270
Val Ile Asp Lys His Asp Trp Glu Leu Val Lys Arg Ile Pro Val Val
        275                 280                 285
Gly Gln Pro Val Phe Val Met Ser Arg Pro Asp Gly Arg Gln Val Trp
        290                 295                 300
Val Asn Phe Ala Phe Pro Asp Asn Gln Thr Val Gln Val Ile Asp Val
305                 310                 315                 320
Lys Asp Phe Asn Ile Val Lys Thr Leu Gln Pro Gly Lys Ala Val Leu
                325                 330                 335
His Met Glu Phe Ser Pro Arg Gly Glu Ala Val Trp Met Ala Val Arg
            340                 345                 350
Asp Glu Asp Arg Val Met Val Tyr Asp Thr Asp Ser Phe Asn Glu Thr
        355                 360                 365
Ala Arg Leu Pro Ala Gln Lys Pro Ser Gly Ile Phe Phe Ser Asn Arg
        370                 375                 380
Ala Asn Gln Leu Gly Leu
385                 390

<210> SEQ ID NO 3
<211> LENGTH: 453
<212> TYPE: DNA
<213> ORGANISM: Methylomonas 16a
<220> FEATURE:
<223> OTHER INFORMATION: ORF2
<220> FEATURE:
<223> OTHER INFORMATION: nirD gene

<400> SEQUENCE: 3
atgctggcat ccttgcacaa gcatttgctg aacgattatc agcaggattt tccgctgagc      60
ccgacaccgt ttctggatat cgccgagcag cttggcgtca cggaaggcga agtgctggcg     120
gcgtttcagg tgttggccga gcagcaaatg atcagccgca tcggccccgt gatcgcgccg     180
```

```
aacgccatcg gcaatagcgc cttggtggcg atggcggtgc cggagcagga tttggcccgt      240
gtcgccgcct tggtgagcgc ctatccggaa gtcaatcata actatgagcg ggaaaaccgc      300
ttcaatttgt ggtttgtgct gatcgcctcc gatcatactc acttgcagcg ggtgattgcc      360
gatatcgaga ctcaaaccgg ttatcaagcc atgctgttgc cgatgctggc cgattatttc      420
atcaacctgg ttttgaact caatctgaac gac                                    453
```

```
<210> SEQ ID NO 4
<211> LENGTH: 151
<212> TYPE: PRT
<213> ORGANISM: Methylomonas 16a
<220> FEATURE:
<223> OTHER INFORMATION: NirD

<400> SEQUENCE: 4

Met Leu Ala Ser Leu His Lys His Leu Leu Asn Asp Tyr Gln Gln Asp
 1               5                  10                  15

Phe Pro Leu Ser Pro Thr Pro Phe Leu Asp Ile Ala Glu Gln Leu Gly
             20                  25                  30

Val Thr Glu Gly Glu Val Leu Ala Ala Phe Gln Val Leu Ala Glu Gln
         35                  40                  45

Gln Met Ile Ser Arg Ile Gly Pro Val Ile Ala Pro Asn Ala Ile Gly
     50                  55                  60

Asn Ser Ala Leu Val Ala Met Ala Val Pro Glu Gln Asp Leu Ala Arg
 65                  70                  75                  80

Val Ala Ala Leu Val Ser Ala Tyr Pro Glu Val Asn His Asn Tyr Glu
                 85                  90                  95

Arg Glu Asn Arg Phe Asn Leu Trp Phe Val Leu Ile Ala Ser Asp His
            100                 105                 110

Thr His Leu Gln Arg Val Ile Ala Asp Ile Glu Thr Gln Thr Gly Tyr
        115                 120                 125

Gln Ala Met Leu Leu Pro Met Leu Ala Asp Tyr Phe Ile Asn Leu Gly
    130                 135                 140

Phe Glu Leu Asn Leu Asn Asp
145                 150
```

```
<210> SEQ ID NO 5
<211> LENGTH: 504
<212> TYPE: DNA
<213> ORGANISM: Methylomonas 16a
<220> FEATURE:
<223> OTHER INFORMATION: ORF3
<220> FEATURE:
<223> OTHER INFORMATION: nirL gene

<400> SEQUENCE: 5
atggatgcct tggattatcg cttgattgcc gccgtgcaag cgggcttacc gcttaccgcg       60
cggccctatg ccgccatcgc cgcgaaattg gacatggacg aacaggacgt catcgcccga      120
ctgggacgtc tgaaaacgga aggtttgatc aggcgctggg gcgtcgtggt caagcaccgg      180
caactaggtt atcgcgccaa tgcgatgatc gtgatggata ttcctgatga tcaagttgcg      240
gaaatgggcc ggcgtgtcag ccagcacagc ttcgtcaatc tgtgttatcg ccgaccacgt      300
caaggcgagg tttggccgta taacctttat tgcatgatac acggcaaaaa tcgcgagacg      360
gttttgcagc aatgggccga tctgcaacaa agttgcggcc tggaagcctg tcggcacgag      420 atttattca gtcgtcgttg tttcaagcag cgtgggctat tttataaagc gcccgtgatt      480
```
gagccattgg agtttagtca tgga 504

<210> SEQ ID NO 6
<211> LENGTH: 168
<212> TYPE: PRT
<213> ORGANISM: Methylomonas 16a
<220> FEATURE:
<223> OTHER INFORMATION: NirL

<400> SEQUENCE: 6

```
Met Asp Ala Leu Asp Tyr Arg Leu Ile Ala Ala Val Gln Ala Gly Leu
 1               5                  10                  15

Pro Leu Thr Ala Arg Pro Tyr Ala Ala Ile Ala Ala Lys Leu Asp Met
            20                  25                  30

Asp Glu Gln Asp Val Ile Ala Arg Leu Gly Arg Leu Lys Thr Glu Gly
        35                  40                  45

Leu Ile Arg Arg Trp Gly Val Val Lys His Arg Gln Leu Gly Tyr
    50                  55                  60

Arg Ala Asn Ala Met Ile Val Met Asp Ile Pro Asp Asp Gln Val Ala
65                  70                  75                  80

Glu Met Gly Arg Arg Val Ser Gln His Ser Phe Val Asn Leu Cys Tyr
                85                  90                  95

Arg Arg Pro Arg Gln Gly Glu Val Trp Pro Tyr Asn Leu Tyr Cys Met
            100                 105                 110

Ile His Gly Lys Asn Arg Glu Thr Val Leu Gln Gln Trp Ala Asp Leu
        115                 120                 125

Gln Gln Ser Cys Gly Leu Glu Ala Cys Arg His Glu Ile Leu Phe Ser
    130                 135                 140

Arg Arg Cys Phe Lys Gln Arg Gly Ala Ile Tyr Lys Ala Pro Val Ile
145                 150                 155                 160

Glu Pro Leu Glu Phe Ser His Gly
                165
```

<210> SEQ ID NO 7
<211> LENGTH: 441
<212> TYPE: DNA
<213> ORGANISM: Methylomonas 16a
<220> FEATURE:
<223> OTHER INFORMATION: ORF4
<220> FEATURE:
<223> OTHER INFORMATION: nirG gene

<400> SEQUENCE: 7
atggatgaca tcgacaaagc catcatcaac cgtttgcaac agggcttgcc gatttgcgag 60
tcgccttata gatatgtcgc cgagcagctt ggtgtggccg aggcggaatt gctggagagg 120
ctgcaaacct tgttgaacca gggcgtttta tcgcgctttg gccgatgta tcacgccgag 180 caaatgggcg cgccttgac cttggcggcg atgaaggtgc caggggagcg tttcgacgaa 240
attgcaggca tcgtcaacgg ctttccggag gtggcgcata actatgcgcg taaccacgcc 300
ttgaacatgt ggtttgtgtt ggcgaccgaa aagccggaac aagtgcaggc ggtcatcgat 360
gccatcgaac ggcaaactgg cttgacggtc tataacatgc cgaaaatcaa ggaatattac 420
gtgggcttgc aactggaggc c 441

<210> SEQ ID NO 8
<211> LENGTH: 147
<212> TYPE: PRT
<213> ORGANISM: Methylomonas 16a
<220> FEATURE:

<223> OTHER INFORMATION: NirG

<400> SEQUENCE: 8

```
Met Asp Asp Ile Asp Lys Ala Ile Ile Asn Arg Leu Gln Gln Gly Leu
1               5                   10                  15

Pro Ile Cys Glu Ser Pro Tyr Arg Tyr Val Ala Glu Gln Leu Gly Val
            20                  25                  30

Ala Glu Ala Glu Leu Leu Glu Arg Leu Gln Thr Leu Leu Asn Gln Gly
        35                  40                  45

Val Leu Ser Arg Phe Gly Pro Met Tyr His Ala Glu Gln Met Gly Gly
    50                  55                  60

Ala Leu Thr Leu Ala Ala Met Lys Val Pro Gly Glu Arg Phe Asp Glu
65                  70                  75                  80

Ile Ala Gly Ile Val Asn Gly Phe Pro Glu Val Ala His Asn Tyr Ala
                85                  90                  95

Arg Asn His Ala Leu Asn Met Trp Phe Val Leu Ala Thr Glu Lys Pro
            100                 105                 110

Glu Gln Val Gln Ala Val Ile Asp Ala Ile Glu Arg Gln Thr Gly Leu
        115                 120                 125

Thr Val Tyr Asn Met Pro Lys Ile Lys Glu Tyr Tyr Val Gly Leu Gln
    130                 135                 140

Leu Glu Ala
145
```

<210> SEQ ID NO 9
<211> LENGTH: 498
<212> TYPE: DNA
<213> ORGANISM: Methylomonas 16a
<220> FEATURE:
<223> OTHER INFORMATION: ORF5
<220> FEATURE:
<223> OTHER INFORMATION: nirH gene

<400> SEQUENCE: 9

```
atggactccg agccagtcaa aataatgatc gacactatcg accgtcaaat catccaggcc      60
acccaggccg gcttgccgct ggtcgcggaa ccttatcagg ccgtcgccga gcaattgggc     120
atcacggctc aagaattgat gctgcgcatg gccgatatgc tggaagctgg catcattcgg     180
cggattgcgg cggtgccgaa tcattacaaa ctgggttatc gtcataacgg catgacggtc     240
tgggatgtcg atgaccggca tgtcgacagc ctggggcagc gcgtcgccga attgccgttc     300
gtcagtcatt gctaccaacg gcctcgccat ttgccggatt ggccgtataa cctgttcgcg     360
atggtgcatg gcaagacgga acaagacgcc gaaaaacaaa ttgccgtgat cgccgaattg     420
ttgggcgagg attgctaccg gcacgcggtg ctgtacagca ccaagatttt gaagaaaacc     480
ggcttgagga ttgcgggg                                                    498
```

<210> SEQ ID NO 10
<211> LENGTH: 166
<212> TYPE: PRT
<213> ORGANISM: Methylomonas 16a
<220> FEATURE:
<223> OTHER INFORMATION: NirH

<400> SEQUENCE: 10

```
Met Asp Ser Glu Pro Val Lys Ile Met Ile Asp Thr Ile Asp Arg Gln
1               5                   10                  15

Ile Ile Gln Ala Thr Gln Ala Gly Leu Pro Leu Val Ala Glu Pro Tyr
            20                  25                  30
```

```
Gln Ala Val Ala Glu Gln Leu Gly Ile Thr Ala Gln Glu Leu Met Leu
        35                  40                  45

Arg Met Ala Asp Met Leu Glu Ala Gly Ile Ile Arg Arg Ile Ala Ala
    50                  55                  60

Val Pro Asn His Tyr Lys Leu Gly Tyr Arg His Asn Gly Met Thr Val
65                  70                  75                  80

Trp Asp Val Asp Asp Arg His Val Asp Ser Leu Gly Gln Arg Val Ala
                85                  90                  95

Glu Leu Pro Phe Val Ser His Cys Tyr Gln Arg Pro Arg His Leu Pro
            100                 105                 110

Asp Trp Pro Tyr Asn Leu Phe Ala Met Val His Gly Lys Thr Glu Gln
        115                 120                 125

Asp Ala Glu Lys Gln Ile Ala Val Ile Ala Glu Leu Leu Gly Glu Asp
    130                 135                 140

Cys Tyr Arg His Ala Val Leu Tyr Ser Thr Lys Ile Leu Lys Lys Thr
145                 150                 155                 160

Gly Leu Arg Ile Ala Gly
                165

<210> SEQ ID NO 11
<211> LENGTH: 1137
<212> TYPE: DNA
<213> ORGANISM: Methylomonas 16a
<220> FEATURE:
<223> OTHER INFORMATION: ORF6
<220> FEATURE:
<223> OTHER INFORMATION: nirJ gene

<400> SEQUENCE: 11
atgtttcgtc tgagtcaata catgcgcgag ctcgtgcatt caacgccgtt gggcaagccg      60
cgcaaaccgt ccggcccggt ggtaatctgg aatctgatcc gtcgctgcaa cctgacttgc     120
aagcattgct ataccacgtc cgccgacatc gattttccgg gtgaactgac gacgccggaa     180
atttatgcgg tgatggacga tttgaaagcc ttcaaggtgc cggtattgat tctgtccggc     240
ggagagccgt tgctgcatcc ggatattttt ccgatttcgc aacgcgccag cgacatgggc     300
ttttacgtgg ccttgtccag caacggcacg ctgatcgaca aaacaatat cgagcaaatc      360 gccgcgatcg attatcaata tattggcgtc agtctggacg gcatgcgcga ggcgcacgac     420
aagttccgcc agaagcaagg ctcttttcgac gcctcgctgg ccggcatccg tttatgccgc     480
gagcatggca tcaaggccgg cgtgcgcttc acgttgacgc gggacaacgc tcacgatttc     540
gatgccttgc tgcagttgat ggacgaggag gacatcgaca aattctatct gtcgcatctg     600
aattacggcg gccgcggcaa taaaaaccgg aaagacgatg ccgagtttca gttgaccccgc    660 aaggtcatgg acgccttgtt cgaaaaggcg ctgagctggg aacagcaagg cctacaccgc     720
gaagtggtca ccggcaacaa cgatgccgat gccgtatatt tcctgcattg ggtcaaacgc     780
cgctttcccg agcgcgccga gcatatccag gccaagttgc agcaatgggg cggcaatgct     840
tccggcgtca acgtagccaa tatcgataat ctgggtaacg tgcatcccga tacctttggg     900
tggcattaca acttgggcag tgtccgccag cggccgtttt ccgagatatg caggatgtg      960 tccgacccat tgatggccgg gctgaaggcc tcgccgcgcc cgctgaaagg ccgctgcggc    1020
acctgtcatt atcaaagcat ttgcaacggc aataccccgcg tccgcgccca caactgacc    1080 ggcgattttt gggctgaaga tccaggctgc tacctggatg acgaggaagt tttcagc       1137

<210> SEQ ID NO 12
```

```
<211> LENGTH: 379
<212> TYPE: PRT
<213> ORGANISM: Methylomonas 16a
<220> FEATURE:
<223> OTHER INFORMATION: Nir J

<400> SEQUENCE: 12

Met Phe Arg Leu Ser Gln Tyr Met Arg Glu Leu Val His Ser Thr Pro
  1               5                  10                  15

Leu Gly Lys Pro Arg Lys Pro Ser Gly Pro Val Val Ile Trp Asn Leu
             20                  25                  30

Ile Arg Arg Cys Asn Leu Thr Cys Lys His Cys Tyr Thr Thr Ser Ala
         35                  40                  45

Asp Ile Asp Phe Pro Gly Glu Leu Thr Thr Pro Glu Ile Tyr Ala Val
     50                  55                  60

Met Asp Asp Leu Lys Ala Phe Lys Val Pro Val Leu Ile Leu Ser Gly
 65                  70                  75                  80

Gly Glu Pro Leu Leu His Pro Asp Ile Phe Pro Ile Ser Gln Arg Ala
                 85                  90                  95

Ser Asp Met Gly Phe Tyr Val Ala Leu Ser Ser Asn Gly Thr Leu Ile
            100                 105                 110

Asp Lys Asn Asn Ile Glu Gln Ile Ala Ala Ile Asp Tyr Gln Tyr Ile
        115                 120                 125

Gly Val Ser Leu Asp Gly Met Arg Glu Ala His Asp Lys Phe Arg Gln
    130                 135                 140

Lys Gln Gly Ser Phe Asp Ala Ser Leu Ala Gly Ile Arg Leu Cys Arg
145                 150                 155                 160

Glu His Gly Ile Lys Ala Gly Val Arg Phe Thr Leu Thr Arg Asp Asn
                165                 170                 175

Ala His Asp Phe Asp Ala Leu Leu Gln Leu Met Asp Glu Glu Asp Ile
            180                 185                 190

Asp Lys Phe Tyr Leu Ser His Leu Asn Tyr Gly Gly Arg Gly Asn Lys
        195                 200                 205

Asn Arg Lys Asp Asp Ala Glu Phe Gln Leu Thr Arg Lys Val Met Asp
    210                 215                 220

Ala Leu Phe Glu Lys Ala Leu Ser Trp Glu Gln Gln Gly Leu His Arg
225                 230                 235                 240

Glu Val Val Thr Gly Asn Asn Asp Ala Asp Ala Val Tyr Phe Leu His
                245                 250                 255

Trp Val Lys Arg Arg Phe Pro Glu Arg Ala Glu His Ile Gln Ala Lys
            260                 265                 270

Leu Gln Gln Trp Gly Gly Asn Ala Ser Gly Val Asn Val Ala Asn Ile
        275                 280                 285

Asp Asn Leu Gly Asn Val His Pro Asp Thr Phe Trp His Tyr Asn
    290                 295                 300

Leu Gly Ser Val Arg Gln Arg Pro Phe Ser Glu Ile Trp Gln Asp Val
305                 310                 315                 320

Ser Asp Pro Leu Met Ala Gly Leu Lys Ala Ser Pro Arg Pro Leu Lys
                325                 330                 335

Gly Arg Cys Gly Thr Cys His Tyr Gln Ser Ile Cys Asn Gly Asn Thr
            340                 345                 350

Arg Val Arg Ala Gln Gln Leu Thr Gly Asp Phe Trp Ala Glu Asp Pro
        355                 360                 365

Gly Cys Tyr Leu Asp Asp Glu Glu Val Phe Ser
    370                 375
```

<210> SEQ ID NO 13
<211> LENGTH: 2760
<212> TYPE: DNA
<213> ORGANISM: Methylomonas 16a
<220> FEATURE:
<223> OTHER INFORMATION: ORF7
<220> FEATURE:
<223> OTHER INFORMATION: nasA gene

<400> SEQUENCE: 13

| | | | | | |
|---|---|---|---|---|---|
| atgtctaaaa | ctgccatcaa | gacgacttgc | ccttattgcg | gcgtcggctg | cggtatcgaa | 60 |
| gccaggtgc | tcgatgccga | aaaccatgtc | gtcaatattg | ccggcgatcc | acagcatcag | 120 |
| tccaatttcg | gccgactgtg | ctccaagggc | gcggcgctgg | gtgataccgt | cggtctggaa | 180 |
| ggccgccttt | tatacccgga | aatcgatggc | cggcgcgtgg | attggcccac | ggtgctggac | 240 |
| cggatcgcgg | ctaaattcaa | tgcgatcatt | gccgagcacg | gcccgacgcg | gtggcgtttt | 300 |
| tatgtgtccg | gacagttgtt | gaccgaggat | tattatgtcg | ccaacaaatt | gatgaagggc | 360 |
| ttcatcgggt | cggcgaatat | cgataccaat | tccaggctgt | gcatgtcctc | ggcggtagtc | 420 |
| ggttacaagc | gtgcgttcgg | cgccgatgcg | gtgccctgta | atttcgagga | tctggaacgg | 480 |
| gcagacttga | tcgtgctggt | cggttccaac | gcggcctggt | gccatccgat | tgcgtttcag | 540 |
| cgcatgcgtc | aggccaagat | agacaatccg | gcgctgaaaa | tcgtactaat | agacccgcgt | 600 |
| caaaccagca | gctgcgatat | cgccgatcgg | catctgggcc | tcaagcccgg | catggacggc | 660 |
| ttgttgttca | atggcttgct | ggtttatctg | gccgaaaccg | gcgcgttgga | tcaggattac | 720 |
| atcgaacgac | actgtgaagg | ttttgccgag | gccttggcga | cggctcgagc | gagcgccgcc | 780 |
| gattttaccg | ttctggccaa | ccgttgcggc | gtggcggcgc | acgatctggc | gcaactgttt | 840 |
| gcctggtttg | ccggtttgga | caaggtcgtg | accgtttatt | cgcaaggcat | caaccagtcc | 900 |
| agttcaggct | ctgataaatg | caacgccatc | atcaattgcc | atctggccag | cggcaaaatc | 960 |
| ggcaaaccgg | gctgcggacc | gttctcgttt | accggccagc | ccaacgcgat | gggcgggcgc | 1020 |
| gaggtcggtg | ggctggcgaa | catgctggcc | gcgcacatgg | atttggaaaa | tccagcgcat | 1080 |
| gtcgatagag | tcgcgcggtt | ttggcaaacc | gacagcgtcg | cccgcaaacc | aggcctgaaa | 1140 |
| gcggtagaaa | ttttcgacgc | catcgccgac | ggtcgcatca | aggccttatg | gatcatggcg | 1200 |
| accaaccccg | tggtatcgat | gccggatgcc | gacaaggtaa | tcgaagcact | taagcaatgc | 1260 |
| gaattttttgc | tggtatcgga | ttgcatcgcc | aacaccgaca | ccgtggagct | ggcgcatgtc | 1320 |
| aaactgccgg | ccaccggctg | gagcgagaag | gacggcaccg | tcaccaatct | ggaacgtcgc | 1380 |
| atctcgcggc | agcggccatt | attccagcct | tcgggcgagg | cgaaaccgga | ttggtggatc | 1440 |
| gtcagccagg | ttgctaagcg | catgggggttt | gccggcttcg | attatcgaaa | cagcgccgaa | 1500 |
| atcttcaagg | aacacgcggc | cttgtccggt | tttgaaaatg | atgcagcgca | ggggggcagg | 1560 |
| gattttgata | tttcaggcct | ggcaacgctg | gatcaggccc | agtttgacgc | cttagtgccg | 1620 |
| atacaatggc | ctgtcacagg | caagactcaa | ggcggaacgg | cgcgcctgtt | cgaagacggt | 1680 |
| cgttttttta | ccgacaccgg | caaggccaga | ttcattgcac | tcgagccgcg | ctcgccaatg | 1740 |
| cacgcccca | caccgatta | tccgctggtc | ttgaataccg | gccgcatccg | cgatcaatgg | 1800 |
| cacacgatga | cccgcaccgc | gctgtccgcg | aagctcaatc | aacacaagcc | ggaaccgttc | 1860 |
| gtggagattc | atccgcagga | tgcgttgcgt | tgggggctca | aagcaaacgc | cctgcccgg | 1920 |
| atcgaaagcc | gttgggggcgg | catgttggcg | cgggtcgacg | tcagcgaggc | tcagcaaccc | 1980 |

-continued

```
ggcagcgtgt tcgtgcccat gcactggacc gcccagctca gcagtcatgg ccgagtcggc    2040
gccgtggtca accctgtcgt ggacccttg tccgggcaac cggaaagcaa gcaaaccccg    2100
gtgcgcatcg cggcttgggc accttgctgg caagcgatgg tattgacgaa atgccattg    2160 gacatcgacg attgcgaata ccacgtcaaa ataagggcc atggcttttg cgctatcat    2220 ttggcggatc aatcccagcg gccagacttg ccggcgtggg gccgcggcat tgtcggcagg    2280
ggggcggcca aacccaatga ttgcgtggaa tatctcgacc tggccgctgg cgattaccgc    2340
tttgccgaga tgcgggatca aacccttcat gcctgcatgt tcattactca taatggggag    2400
ttgccggacc ctggctggct ggccagccta ttcggcaaac cgagattgac ccgcaaggaa    2460
cgcttcaacc tgctcagcgg cgtgccgccg caaggggaaa tcgatagcgg caaaacgatc    2520
tgctcctgct tcaacgtcgg cgaaaaaacc atcgtgcaag ccattcaaac ccgacatttg    2580
agctgtgtaa cagatatagg caactgcctg catgcgggaa cgggttgtgg ttcgtgttta    2640
ccggaattaa aaagcatttt ggcccacgcc aaaacgatcg atcctgcctc gctgcccatt    2700
cagccaactc aaatcccgcc ggcatcggag gggaaggagg aagccttttt ttcaggtcaa    2760
```

<210> SEQ ID NO 14
<211> LENGTH: 920
<212> TYPE: PRT
<213> ORGANISM: Methylomonas 16a
<220> FEATURE:
<223> OTHER INFORMATION: NasA

<400> SEQUENCE: 14

```
Met Ser Lys Thr Ala Ile Lys Thr Thr Cys Pro Tyr Cys Gly Val Gly
  1               5                  10                  15

Cys Gly Ile Glu Ala Arg Val Leu Asp Ala Glu Asn His Val Val Asn
             20                  25                  30

Ile Ala Gly Asp Pro Gln His Gln Ser Asn Phe Gly Arg Leu Cys Ser
         35                  40                  45

Lys Gly Ala Ala Leu Gly Asp Thr Val Gly Leu Glu Gly Arg Leu Leu
     50                  55                  60

Tyr Pro Glu Ile Asp Gly Arg Val Asp Trp Pro Thr Val Leu Asp
 65                  70                  75                  80

Arg Ile Ala Ala Lys Phe Asn Ala Ile Ile Ala Glu His Gly Pro Asp
                 85                  90                  95

Ala Val Ala Phe Tyr Val Ser Gly Gln Leu Leu Thr Glu Asp Tyr Tyr
            100                 105                 110

Val Ala Asn Lys Leu Met Lys Gly Phe Ile Gly Ser Ala Asn Ile Asp
        115                 120                 125

Thr Asn Ser Arg Leu Cys Met Ser Ser Ala Val Val Gly Tyr Lys Arg
    130                 135                 140

Ala Phe Gly Ala Asp Ala Val Pro Cys Asn Phe Glu Asp Leu Glu Arg
145                 150                 155                 160

Ala Asp Leu Ile Val Leu Val Gly Ser Asn Ala Ala Trp Cys His Pro
                165                 170                 175

Ile Ala Phe Gln Arg Met Arg Gln Ala Lys Ile Asp Asn Pro Ala Leu
            180                 185                 190

Lys Ile Val Leu Ile Asp Pro Arg Gln Thr Ser Ser Cys Asp Ile Ala
        195                 200                 205

Asp Arg His Leu Ala Ile Lys Pro Gly Met Asp Gly Leu Leu Phe Asn
    210                 215                 220

Gly Leu Leu Val Tyr Leu Ala Glu Thr Gly Ala Leu Asp Gln Asp Tyr
```

```
              225                 230                 235                 240

Ile Glu Arg His Cys Glu Gly Phe Ala Glu Ala Leu Ala Thr Ala Arg
                245                 250                 255

Ala Ser Ala Ala Asp Phe Thr Val Leu Ala Asn Arg Cys Gly Val Ala
                260                 265                 270

Ala His Asp Leu Ala Gln Leu Phe Ala Trp Phe Ala Gly Leu Asp Lys
                275                 280                 285

Val Val Thr Val Tyr Ser Gln Gly Ile Asn Gln Ser Ser Gly Ser
                290                 295                 300

Asp Lys Cys Asn Ala Ile Ile Asn Cys His Leu Ala Ser Gly Lys Ile
305                 310                 315                 320

Gly Lys Pro Gly Cys Gly Pro Phe Ser Phe Thr Gly Gln Pro Asn Ala
                325                 330                 335

Met Gly Gly Arg Glu Val Gly Leu Ala Asn Met Leu Ala Ala His
                340                 345                 350

Met Asp Leu Glu Asn Pro Ala His Val Asp Arg Val Ala Arg Phe Trp
                355                 360                 365

Gln Thr Asp Ser Val Ala Arg Lys Pro Gly Leu Lys Ala Val Glu Ile
                370                 375                 380

Phe Asp Ala Ile Ala Asp Gly Arg Ile Lys Ala Leu Trp Ile Met Ala
385                 390                 395                 400

Thr Asn Pro Val Val Ser Met Pro Asp Ala Asp Lys Val Ile Glu Ala
                405                 410                 415

Leu Lys Gln Cys Glu Phe Leu Leu Val Ser Asp Cys Ile Ala Asn Thr
                420                 425                 430

Asp Thr Val Glu Leu Ala His Val Lys Leu Pro Ala Thr Gly Trp Ser
                435                 440                 445

Glu Lys Asp Gly Thr Val Thr Asn Leu Glu Arg Arg Ile Ser Arg Gln
450                 455                 460

Arg Pro Leu Phe Gln Pro Ser Gly Glu Ala Lys Pro Asp Trp Trp Ile
465                 470                 475                 480

Val Ser Gln Val Ala Lys Arg Met Gly Phe Ala Gly Phe Asp Tyr Arg
                485                 490                 495

Asn Ser Ala Glu Ile Phe Lys Glu His Ala Ala Leu Ser Gly Phe Glu
                500                 505                 510

Asn Asp Ala Ala Gln Gly Gly Arg Asp Phe Asp Ile Ser Gly Leu Ala
                515                 520                 525

Thr Leu Asp Gln Ala Gln Phe Asp Ala Leu Val Pro Ile Gln Trp Pro
                530                 535                 540

Val Thr Gly Lys Thr Gln Gly Gly Thr Ala Arg Leu Phe Glu Asp Gly
545                 550                 555                 560

Arg Phe Phe Thr Asp Thr Gly Lys Ala Arg Phe Ile Ala Leu Glu Pro
                565                 570                 575

Arg Ser Pro Met His Ala Pro Thr Pro Asp Tyr Pro Leu Val Leu Asn
                580                 585                 590

Thr Gly Arg Ile Arg Asp Gln Trp His Thr Met Thr Arg Thr Ala Leu
                595                 600                 605

Ser Ala Lys Leu Asn Gln His Lys Pro Glu Pro Phe Val Glu Ile His
                610                 615                 620

Pro Gln Asp Ala Leu Arg Trp Gly Leu Lys Ala Asn Ala Leu Ala Arg
625                 630                 635                 640

Ile Glu Ser Arg Trp Gly Gly Met Leu Ala Arg Val Asp Val Ser Glu
                645                 650                 655
```

```
Ala Gln Gln Pro Gly Ser Val Phe Val Pro Met His Trp Thr Ala Gln
                660                 665                 670

Leu Ser Ser His Gly Arg Val Gly Ala Val Asn Pro Val Val Asp
            675                 680                 685

Pro Leu Ser Gly Gln Pro Glu Ser Lys Gln Thr Pro Val Arg Ile Ala
        690                 695                 700

Ala Trp Ala Pro Cys Trp Gln Ala Met Val Leu Thr Lys Met Pro Leu
705                 710                 715                 720

Asp Ile Asp Asp Cys Glu Tyr His Val Lys Ile Arg Gly His Gly Phe
                725                 730                 735

Trp Arg Tyr His Leu Ala Asp Gln Ser Gln Arg Pro Asp Leu Pro Ala
            740                 745                 750

Trp Gly Arg Gly Ile Val Gly Arg Gly Ala Ala Lys Pro Asn Asp Cys
        755                 760                 765

Val Glu Tyr Leu Asp Leu Ala Ala Gly Asp Tyr Arg Phe Ala Glu Met
770                 775                 780

Arg Asp Gln Thr Leu His Ala Cys Met Phe Ile Thr His Asn Gly Glu
785                 790                 795                 800

Leu Pro Asp Pro Gly Trp Leu Ala Ser Leu Phe Gly Lys Pro Arg Leu
                805                 810                 815

Thr Arg Lys Glu Arg Phe Asn Leu Leu Ser Gly Val Pro Pro Gln Gly
            820                 825                 830

Glu Ile Asp Ser Gly Lys Thr Ile Cys Ser Cys Phe Asn Val Gly Glu
        835                 840                 845

Lys Thr Ile Val Gln Ala Ile Gln Thr Arg His Leu Ser Cys Val Thr
850                 855                 860

Asp Ile Gly Asn Cys Leu His Ala Gly Thr Gly Cys Gly Ser Cys Leu
865                 870                 875                 880

Pro Glu Leu Lys Ser Ile Leu Ala His Ala Lys Thr Ile Asp Pro Ala
                885                 890                 895

Ser Leu Pro Ile Gln Pro Thr Gln Ile Pro Pro Ala Ser Glu Gly Lys
            900                 905                 910

Glu Glu Ala Phe Phe Ser Gly Gln
        915                 920

<210> SEQ ID NO 15
<211> LENGTH: 642
<212> TYPE: DNA
<213> ORGANISM: Methylomonas 16a
<220> FEATURE:
<223> OTHER INFORMATION: ORF8
<220> FEATURE:
<223> OTHER INFORMATION: norC gene

<400> SEQUENCE: 15
atggcaacga aaccgaacat tcacatcaac ctggaggtcg tcatgactga gcaagtcccg    60
cgctgggcgt cggaaacatt ctggaaaaaa accgcgatct gggtcaccgg cggatcgttc   120
gtgttgctgg tgatcttgac cttcgactcg ctggcgaaga tttccgctgg cggccccagg   180
gtgccggcct tcgacgtcat caacaaagac gtcagttacc gtttcgacaa ggaaaaacaa   240
cgctaccaac cagtgatcgg cgacgacgcc cctctgtttg caaaaccct  gagcgaggaa   300 gaagccgaaa aactggtcga cctgggcaag aaaaccgtgc aggccaagaa ctgcatgaac   360 tgccatacccc tgctcggcaa tggcgcttat tatgcgcccg acttgaccaa ggcctggctg   420
gaccagggct ggatcgccaa ggagtcgcgc gagcaaatga tggtcaattt cctgctcgat   480
```

-continued

```
cccgagaaaa atgcccgcac cttcggctcc aaccgcaaga tgccgaatct cgacatcacg    540
caacaggagg ccgagggcat cgtcgccttt ttgaaatgga tggcatccat cgacaccaat    600
ggttttccgc ataatttcat cgcgctgggc gaagaggaca aa                       642
```

```
<210> SEQ ID NO 16
<211> LENGTH: 214
<212> TYPE: PRT
<213> ORGANISM: Methylomonas 16a
<220> FEATURE:
<223> OTHER INFORMATION: NorC

<400> SEQUENCE: 16
```

| Met | Ala | Thr | Lys | Pro | Asn | Ile | His | Ile | Asn | Leu | Glu | Val | Val | Met | Thr |
|---|---|---|---|---|---|---|---|---|---|---|---|---|---|---|---|
| 1 | | | | 5 | | | | | 10 | | | | | 15 | |

| Glu | Gln | Val | Pro | Arg | Trp | Ala | Ser | Glu | Thr | Phe | Trp | Lys | Lys | Thr | Ala |
|---|---|---|---|---|---|---|---|---|---|---|---|---|---|---|---|
| | | | 20 | | | | | 25 | | | | | 30 | | |

| Ile | Trp | Val | Thr | Gly | Gly | Ser | Phe | Val | Leu | Leu | Val | Ile | Leu | Thr | Phe |
|---|---|---|---|---|---|---|---|---|---|---|---|---|---|---|---|
| | | | 35 | | | | | 40 | | | | | 45 | | |

| Asp | Ser | Leu | Ala | Lys | Ile | Ser | Ala | Gly | Gly | Pro | Arg | Val | Pro | Ala | Phe |
|---|---|---|---|---|---|---|---|---|---|---|---|---|---|---|---|
| | 50 | | | | | 55 | | | | | 60 | | | | |

| Asp | Val | Ile | Asn | Lys | Asp | Val | Ser | Tyr | Arg | Phe | Asp | Lys | Glu | Lys | Gln |
|---|---|---|---|---|---|---|---|---|---|---|---|---|---|---|---|
| 65 | | | | | 70 | | | | | 75 | | | | | 80 |

| Arg | Tyr | Gln | Pro | Val | Ile | Gly | Asp | Asp | Ala | Pro | Leu | Phe | Gly | Lys | Thr |
|---|---|---|---|---|---|---|---|---|---|---|---|---|---|---|---|
| | | | | 85 | | | | | 90 | | | | | 95 | |

| Leu | Ser | Glu | Glu | Glu | Ala | Glu | Lys | Leu | Val | Asp | Leu | Gly | Lys | Lys | Thr |
|---|---|---|---|---|---|---|---|---|---|---|---|---|---|---|---|
| | | | 100 | | | | | 105 | | | | | 110 | | |

| Val | Gln | Ala | Lys | Asn | Cys | Met | Asn | Cys | His | Thr | Leu | Leu | Gly | Asn | Gly |
|---|---|---|---|---|---|---|---|---|---|---|---|---|---|---|---|
| | | | 115 | | | | | 120 | | | | | 125 | | |

| Ala | Tyr | Tyr | Ala | Pro | Asp | Leu | Thr | Lys | Ala | Trp | Leu | Asp | Gln | Gly | Trp |
|---|---|---|---|---|---|---|---|---|---|---|---|---|---|---|---|
| | 130 | | | | | 135 | | | | | 140 | | | | |

| Ile | Ala | Lys | Glu | Ser | Arg | Glu | Gln | Met | Met | Val | Asn | Phe | Leu | Leu | Asp |
|---|---|---|---|---|---|---|---|---|---|---|---|---|---|---|---|
| 145 | | | | | 150 | | | | | 155 | | | | | 160 |

| Pro | Glu | Lys | Asn | Ala | Arg | Thr | Phe | Gly | Ser | Asn | Arg | Lys | Met | Pro | Asn |
|---|---|---|---|---|---|---|---|---|---|---|---|---|---|---|---|
| | | | | 165 | | | | | 170 | | | | | 175 | |

| Leu | Asp | Ile | Thr | Gln | Gln | Glu | Ala | Glu | Gly | Ile | Val | Ala | Phe | Leu | Lys |
|---|---|---|---|---|---|---|---|---|---|---|---|---|---|---|---|
| | | | 180 | | | | | 185 | | | | | 190 | | |

| Trp | Met | Ala | Ser | Ile | Asp | Thr | Asn | Gly | Phe | Pro | His | Asn | Phe | Ile | Ala |
|---|---|---|---|---|---|---|---|---|---|---|---|---|---|---|---|
| | | | 195 | | | | | 200 | | | | | 205 | | |

| Leu | Gly | Glu | Glu | Asp | Lys |
|---|---|---|---|---|---|
| | | | | | 210 |

```
<210> SEQ ID NO 17
<211> LENGTH: 1503
<212> TYPE: DNA
<213> ORGANISM: Methylomonas 16a
<220> FEATURE:
<223> OTHER INFORMATION: ORF9
<220> FEATURE:
<223> OTHER INFORMATION: norB gene

<400> SEQUENCE: 17
```

```
atgacgctac aagcctatca agaaaaagcc gctgtctgct gggccggttg caagcaacgc    60
cacgccgact tcatggccaa tccgcatttg accggcggcc aaaagctggc ggtgcattac   120
ttcaccgtcg ccatggtgct gttcatggcg caattgctgt tcggcctgct ggccggcctg   180
caattcatct tcccgagttt tttatacgaa atcctggatt tcaacgtcaa ccgcatggtg   240
```

-continued

```
cacatcaatg ccatggtggt gtggatgctg tacggctttt tgggctcggt gtactggttt      300
ctggaagacg agagcggcgt cgagatcgtc ggcttgaaat gggggcaact ggcgttttgg      360
gtgctgaccg gtgcggtcgc gctggtcgtg ctggtgtatt tgttcatcca gatcggcgcc      420
ggcaacgaca cttcgctgtg gctgatcaac gaaggccgcg aatacatcga agccccgcgc      480
tgggccgaca tcggcatcgt cgccgtggta ttgaccttct tttacaacgt cgccgccacc      540
ttcgccaaag gcaaatggtc cggcattgcc ggcgtgttga ccctggatct ggtggccctg      600
gccggcttgt atctggccgg catgttctac gtcaccaata tttcggtcga ccaatactgg      660
tggtggtggg tgatccatct atgggtcgaa gcgacctggg aagtgctggt tggctgcatc      720
atggcctgga gcctgatgaa gctgctgggc gtgcgccgcc aggtcgtaca acttggttg      780
tacatcgaag ttgctttgat gttcggctcc ggcattcttg gctgggtca tcactatttc      840
tggatcggca cgccggaata ctggttcagc atcggcggct tcttctcggc gctggaaccg      900
attccgctgg tagcaatggt cgtgcattcc atttacgatt ccggcgtgca aagtttaaa      960
aacagcaatc accccgccct ggcctggatc atcgcccata ctttcggcaa cttcctgggc     1020
gccggcgttt ggggattcat gcacacgctg ccgcaaatca acctgtacac ccacggcacg     1080
caatggtcgg cctcgcacgg ccacctggcc ttcttcggcg cctatgcgac catcaacatc     1140
gccttcttct acctggcggc gcagcaggcg cgcggcaacg tctggatggg cggtgacttg     1200
atcaacggct ggcgctggaa agcggcggcg attttgctaa atctgggcgt gttgggcatg     1260
accgtggcgc tattgatcgc cggttacgag caatcgttta tcgaacgcgc cgtcgaaggc     1320
tcgacctggg ccggttactt cgccgcgcaa aaccaccgt ggttcatgca agccatggtc     1380
tggcgcatgg tattcggctt gatgacggcc gtcggcggcg gcctgttgtt ctgggacttg     1440
ctggaaatcg gcaaaggcga acagcggccc gcggcggtga ttgccggtgg aacggttgcg     1500
gaa                                                                    1503
```

<210> SEQ ID NO 18
<211> LENGTH: 501
<212> TYPE: PRT
<213> ORGANISM: Methylomonas 16a
<220> FEATURE:
<223> OTHER INFORMATION: NorB

<400> SEQUENCE: 18

```
Met Thr Leu Gln Ala Tyr Gln Glu Lys Ala Ala Val Cys Trp Ala Gly
 1               5                  10                  15

Cys Lys Gln Arg His Ala Asp Phe Met Ala Asn Pro His Leu Thr Gly
             20                  25                  30

Gly Gln Lys Leu Ala Val His Tyr Phe Thr Val Ala Met Val Leu Phe
         35                  40                  45

Met Ala Gln Leu Leu Phe Gly Leu Leu Ala Gly Leu Gln Phe Ile Phe
     50                  55                  60

Pro Ser Phe Leu Tyr Glu Ile Leu Asp Phe Asn Val Asn Arg Met Val
 65                  70                  75                  80

His Ile Asn Ala Met Val Val Trp Met Leu Tyr Gly Phe Leu Gly Ser
                 85                  90                  95

Val Tyr Trp Phe Leu Glu Asp Glu Ser Gly Val Glu Ile Val Gly Leu
            100                 105                 110

Lys Trp Gly Gln Leu Ala Phe Trp Val Leu Thr Gly Ala Val Ala Leu
        115                 120                 125

Val Val Leu Val Tyr Leu Phe Ile Gln Ile Gly Ala Gly Asn Asp Thr
```

-continued

```
            130                 135                 140
Ser Leu Trp Leu Ile Asn Glu Gly Arg Glu Tyr Ile Glu Ala Pro Arg
145                 150                 155                 160

Trp Ala Asp Ile Gly Ile Val Ala Val Val Leu Thr Phe Phe Tyr Asn
                165                 170                 175

Val Ala Ala Thr Phe Ala Lys Gly Lys Trp Ser Gly Ile Ala Gly Val
                180                 185                 190

Leu Thr Leu Asp Leu Val Ala Leu Ala Gly Leu Tyr Leu Ala Gly Met
                195                 200                 205

Phe Tyr Val Thr Asn Ile Ser Val Asp Gln Tyr Trp Trp Trp Trp Val
210                 215                 220

Ile His Leu Trp Val Glu Ala Thr Trp Glu Val Leu Val Gly Cys Ile
225                 230                 235                 240

Met Ala Trp Ser Leu Met Lys Leu Leu Gly Val Arg Arg Gln Val Val
                245                 250                 255

Gln Thr Trp Leu Tyr Ile Glu Val Ala Leu Met Phe Gly Ser Gly Ile
                260                 265                 270

Leu Gly Leu Gly His His Tyr Phe Trp Ile Gly Thr Pro Glu Tyr Trp
                275                 280                 285

Phe Ser Ile Gly Gly Phe Phe Ser Ala Leu Glu Pro Ile Pro Leu Val
                290                 295                 300

Ala Met Val Val His Ser Ile Tyr Asp Ser Gly Val His Lys Phe Lys
305                 310                 315                 320

Asn Ser Asn His Pro Ala Leu Ala Trp Ile Ala His Thr Phe Gly
                325                 330                 335

Asn Phe Leu Gly Ala Gly Val Trp Gly Phe Met His Thr Leu Pro Gln
                340                 345                 350

Ile Asn Leu Tyr Thr His Gly Thr Gln Trp Ser Ala Ser His Gly His
                355                 360                 365

Leu Ala Phe Phe Gly Ala Tyr Ala Thr Ile Asn Ile Ala Phe Phe Tyr
370                 375                 380

Leu Ala Ala Gln Gln Ala Arg Gly Asn Val Trp Met Gly Gly Asp Leu
385                 390                 395                 400

Ile Asn Gly Trp Arg Trp Lys Ala Ala Ile Leu Leu Asn Leu Gly
                405                 410                 415

Val Leu Gly Met Thr Val Ala Leu Leu Ile Ala Gly Tyr Glu Gln Ser
                420                 425                 430

Phe Ile Glu Arg Ala Val Glu Gly Ser Thr Trp Ala Gly Tyr Phe Ala
                435                 440                 445

Ala Gln Asn His Pro Trp Phe Met Gln Ala Met Val Trp Arg Met Val
450                 455                 460

Phe Gly Leu Met Thr Ala Val Gly Gly Leu Leu Phe Trp Asp Leu
465                 470                 475                 480

Leu Glu Ile Gly Lys Gly Glu Gln Arg Pro Ala Ala Val Ile Ala Gly
                485                 490                 495

Gly Thr Val Ala Glu
            500

<210> SEQ ID NO 19
<211> LENGTH: 2253
<212> TYPE: DNA
<213> ORGANISM: Methylomonas 16a
<220> FEATURE:
<223> OTHER INFORMATION: ORF10
<220> FEATURE:
```

<223> OTHER INFORMATION: norZ gene

<400> SEQUENCE: 19

| | | | | | |
|---|---|---|---|---|---|
| atgacaaaaa | ctcctgattt | gtctccttgg | tggctgcgca | cggtgctgat | cgtgatggtg | 60 |
| ctgggctttg | caggcctgat | cgtcatcaca | tcgctggcct | atcgtaatgc | tccgccgatt | 120 |
| ccggcccaaa | tcgttgatgc | acaaggtgtt | cgcctgtttt | ccggtgacga | aatcaaagaa | 180 |
| ggccaggcta | tctttctcaa | atacggttg | atgaacaacg | gcagtatctg | gggtcatggc | 240 |
| gcatacttgg | ggccagatta | ttcggccgag | gcattgcacc | gaatcggcga | gaacaccgcc | 300 |
| actatcattg | cccagcagca | ataccaacag | ccactttcct | cactcacgcc | cggccaattg | 360 |
| gccgccgtgt | atgcacaaac | cgcagtcgag | ctaaagacca | atcattatga | tgccgccagc | 420 |
| gcaacgttgc | gtctgaccgt | gccggagaca | tccgcctatc | gtaagcagat | cgcttattgg | 480 |
| acggattatt | tcctgaatcc | tgaacggaat | ggcggactca | acgtggatt | gatcagcgat | 540 |
| ccgactgaac | tgcgccagtt | taccgccttc | atcacatgga | ctgcctgggc | ctcggtggcc | 600 |
| aaccgccccg | gcgagaacta | ctcctacacc | aacaattttc | catacgaccc | cagcgtcggg | 660 |
| aatatgcccg | ttccggtgc | gctgttatgg | agtgcgttga | gccttatcgt | gctgctggcc | 720 |
| ggtattggaa | tcgtacttct | gatgtttgga | aaattcgatt | atcttggctg | gattagcaca | 780 |
| ggacatcatg | tacatcctca | tctgttgcct | gggcaagcca | gtgccggtca | actagcactg | 840 |
| gtgaaatttt | tcgtggtggt | ggcgctgctg | tttcttgctc | agaccttggt | gggcggtgca | 900 |
| acggcgcact | atcgcgccga | tccaggcagt | ttttacggcc | ttgagctgga | gaagctattt | 960 |
| cccagcaatc | tgatgcgcac | ctggcatcta | caaaccgcgg | ttttctggat | tgccaccgct | 1020 |
| tttgtcgccg | cagccttgtt | tctcggtcgt | tcactgcgca | atgatgaacc | tcgctggttc | 1080 |
| gcgggctggg | ttcatctgct | gttcggtgct | ttcgccgtgg | tcataggcgg | tagcctgtta | 1140 |
| ggcgagtggg | cggggatttc | acaaatgctg | gatcaatggt | ggttctggct | tggcaaccag | 1200 |
| ggttgggaat | acctggagct | cggccgtctg | tggcagtacc | tgcttatcgc | cggtctgctg | 1260 |
| gcgtggttta | cgcttttatt | taagttgcta | cagcctgata | ccctgaacga | ctcagaagcg | 1320 |
| aaaccttag | tcaggctgtt | cctgctagct | tccttggcga | ttccgctgtt | ctacatcccg | 1380 |
| gcactcttct | tcggcgcaaa | gaccaacttc | acagtggtcg | atacctggcg | cttctggatc | 1440 |
| attcatttat | gggtcgaagg | tttctttgaa | ttctttgcca | ccacgctggt | ggcgctgctg | 1500 |
| ttttatcaac | tgggtcttac | ccagcgcaac | gttgcgcttc | gagtgattta | cctcgacgcc | 1560 |
| atcctctatt | tcgtcggcgg | cctgattggt | accggccatc | actggtattt | taccggccag | 1620 |
| agcagcgtca | acatggcgct | gtcggcaatg | gtctcggtac | tggaagtagt | gcccttgacg | 1680 |
| ctgctgactc | tggacgcctg | ggatttcgtg | cgcaccacac | gcgctgactg | cgacgtctgc | 1740 |
| ggcaaaccgg | tagccatacc | gcataaatgg | acgttctatt | tcttgatggc | cgtcggcttc | 1800 |
| tggaatttcg | tcggtgccgg | catcttcggc | tttctaatca | acctgcctat | cgtcagctat | 1860 |
| tatgaagtcg | gaacccaact | gacacccaac | catggccatg | ccgcgatgat | ggggtattc | 1920 |
| ggcatgctgg | cactggcact | gatggtattc | gtgttcgcc | agaccagctc | cgatttgcgc | 1980 |
| tgggtcgaca | tcgagaaata | cgtaagggtc | ggattttggg | gctccaatgt | tggcctggct | 2040 |
| ctgatgttaa | tcatgagctt | gttccccagt | ggcgtgttgc | aagtttggga | tgtcgttcag | 2100 |
| catggatact | ggcatgcgcg | cagccttgat | tacatcggca | gcgaaaggtc | gcgcctgatc | 2160 |
| gaatggctac | gtctgcccgg | tgatctggta | tttatcctgt | ttggcgccat | accgttggca | 2220 |
| atcgcatcca | tcaaaggctg | gctggatgtg | cat | | | 2253 |

<210> SEQ ID NO 20
<211> LENGTH: 751
<212> TYPE: PRT
<213> ORGANISM: Methylomonas 16a
<220> FEATURE:
<223> OTHER INFORMATION: NorZ

<400> SEQUENCE: 20

| | | | | | | | | | | | | | | |
|---|---|---|---|---|---|---|---|---|---|---|---|---|---|---|
| Met | Thr | Lys | Thr | Pro | Asp | Leu | Ser | Pro | Trp | Trp | Leu | Arg | Thr | Val | Leu |
| 1 | | | | 5 | | | | | 10 | | | | | 15 | |
| Ile | Val | Met | Val | Leu | Gly | Phe | Ala | Gly | Leu | Ile | Val | Ile | Thr | Ser | Leu |
| | | | 20 | | | | | 25 | | | | | 30 | | |
| Ala | Tyr | Arg | Asn | Ala | Pro | Pro | Ile | Pro | Ala | Gln | Ile | Val | Asp | Ala | Gln |
| | | 35 | | | | | 40 | | | | | 45 | | | |
| Gly | Val | Arg | Leu | Phe | Ser | Gly | Asp | Glu | Ile | Lys | Glu | Gly | Gln | Ala | Ile |
| | 50 | | | | | 55 | | | | | 60 | | | | |
| Phe | Leu | Lys | Tyr | Gly | Leu | Met | Asn | Asn | Gly | Ser | Ile | Trp | Gly | His | Gly |
| 65 | | | | | 70 | | | | | 75 | | | | | 80 |
| Ala | Tyr | Leu | Gly | Pro | Asp | Tyr | Ser | Ala | Glu | Ala | Leu | His | Arg | Ile | Gly |
| | | | | 85 | | | | | 90 | | | | | 95 | |
| Glu | Asn | Thr | Ala | Thr | Ile | Ile | Ala | Gln | Gln | Gln | Tyr | Gln | Gln | Pro | Leu |
| | | | 100 | | | | | 105 | | | | | 110 | | |
| Ser | Ser | Leu | Thr | Pro | Gly | Gln | Leu | Ala | Ala | Val | Tyr | Ala | Gln | Thr | Ala |
| | | 115 | | | | | 120 | | | | | 125 | | | |
| Val | Glu | Leu | Lys | Thr | Asn | His | Tyr | Asp | Ala | Ala | Ser | Ala | Thr | Leu | Arg |
| | 130 | | | | | 135 | | | | | 140 | | | | |
| Leu | Thr | Val | Pro | Glu | Thr | Ser | Ala | Tyr | Arg | Lys | Gln | Ile | Ala | Tyr | Trp |
| 145 | | | | | 150 | | | | | 155 | | | | | 160 |
| Thr | Asp | Tyr | Phe | Leu | Asn | Pro | Glu | Arg | Asn | Gly | Gly | Leu | Lys | Arg | Gly |
| | | | | 165 | | | | | 170 | | | | | 175 | |
| Leu | Ile | Ser | Asp | Pro | Thr | Glu | Leu | Arg | Gln | Phe | Thr | Ala | Phe | Ile | Thr |
| | | | 180 | | | | | 185 | | | | | 190 | | |
| Trp | Thr | Ala | Trp | Ala | Ser | Val | Ala | Asn | Arg | Pro | Gly | Glu | Asn | Tyr | Ser |
| | | 195 | | | | | 200 | | | | | 205 | | | |
| Tyr | Thr | Asn | Asn | Phe | Pro | Tyr | Asp | Pro | Ser | Val | Gly | Asn | Met | Pro | Val |
| | 210 | | | | | 215 | | | | | 220 | | | | |
| Pro | Gly | Ala | Leu | Leu | Trp | Ser | Ala | Leu | Ser | Leu | Ile | Val | Leu | Leu | Ala |
| 225 | | | | | 230 | | | | | 235 | | | | | 240 |
| Gly | Ile | Gly | Ile | Val | Leu | Leu | Met | Phe | Gly | Lys | Phe | Asp | Tyr | Leu | Gly |
| | | | | 245 | | | | | 250 | | | | | 255 | |
| Trp | Ile | Ser | Thr | Gly | His | His | Val | His | Pro | His | Leu | Leu | Pro | Gly | Gln |
| | | | 260 | | | | | 265 | | | | | 270 | | |
| Ala | Ser | Ala | Gly | Gln | Leu | Ala | Leu | Val | Lys | Phe | Phe | Val | Val | Ala |
| | | 275 | | | | | 280 | | | | | 285 | | | |
| Leu | Leu | Phe | Leu | Ala | Gln | Thr | Leu | Val | Gly | Gly | Ala | Thr | Ala | His | Tyr |
| | 290 | | | | | 295 | | | | | 300 | | | | |
| Arg | Ala | Asp | Pro | Gly | Ser | Phe | Tyr | Gly | Leu | Glu | Leu | Glu | Lys | Leu | Phe |
| 305 | | | | | 310 | | | | | 315 | | | | | 320 |
| Pro | Ser | Asn | Leu | Met | Arg | Thr | Trp | His | Leu | Gln | Thr | Ala | Val | Phe | Trp |
| | | | | 325 | | | | | 330 | | | | | 335 | |
| Ile | Ala | Thr | Ala | Phe | Val | Ala | Ala | Leu | Phe | Leu | Gly | Arg | Ser | Leu |
| | | | 340 | | | | | 345 | | | | | 350 | | |
| Arg | Asn | Asp | Glu | Pro | Arg | Trp | Phe | Ala | Gly | Trp | Val | His | Leu | Leu | Phe |
| | | 355 | | | | | 360 | | | | | 365 | | | |

```
Gly Ala Phe Ala Val Val Ile Gly Gly Ser Leu Leu Gly Glu Trp Ala
    370                 375                 380

Gly Ile Ser Gln Met Leu Asp Gln Trp Trp Phe Trp Leu Gly Asn Gln
385                 390                 395                 400

Gly Trp Glu Tyr Leu Glu Leu Gly Arg Leu Trp Gln Tyr Leu Leu Ile
            405                 410                 415

Ala Gly Leu Leu Ala Trp Phe Thr Leu Leu Phe Lys Leu Leu Gln Pro
        420                 425                 430

Asp Thr Leu Asn Asp Ser Glu Ala Lys Pro Leu Val Arg Leu Phe Leu
        435                 440                 445

Leu Ala Ser Leu Ala Ile Pro Leu Phe Tyr Ile Pro Ala Leu Phe Phe
    450                 455                 460

Gly Ala Lys Thr Asn Phe Thr Val Val Asp Thr Trp Arg Phe Trp Ile
465                 470                 475                 480

Ile His Leu Trp Val Glu Gly Phe Phe Glu Phe Phe Ala Thr Thr Leu
            485                 490                 495

Val Ala Leu Leu Phe Tyr Gln Leu Gly Leu Thr Gln Arg Asn Val Ala
        500                 505                 510

Leu Arg Val Ile Tyr Leu Asp Ala Ile Leu Tyr Phe Val Gly Gly Leu
    515                 520                 525

Ile Gly Thr Gly His His Trp Tyr Phe Thr Gly Gln Ser Ser Val Asn
    530                 535                 540

Met Ala Leu Ser Ala Met Val Ser Val Leu Glu Val Val Pro Leu Thr
545                 550                 555                 560

Leu Leu Thr Leu Asp Ala Trp Asp Phe Val Arg Thr Arg Ala Asp
            565                 570                 575

Cys Asp Val Cys Gly Lys Pro Val Ala Ile Pro His Lys Trp Thr Phe
                580                 585                 590

Tyr Phe Leu Met Ala Val Gly Phe Trp Asn Phe Val Gly Ala Gly Ile
            595                 600                 605

Phe Gly Phe Leu Ile Asn Leu Pro Ile Val Ser Tyr Tyr Glu Val Gly
    610                 615                 620

Thr Gln Leu Thr Pro Asn His Gly His Ala Ala Met Met Gly Val Phe
625                 630                 635                 640

Gly Met Leu Ala Leu Ala Leu Met Val Phe Val Leu Arg Gln Thr Ser
                645                 650                 655

Ser Asp Leu Arg Trp Val Asp Ile Glu Lys Tyr Val Arg Val Gly Phe
            660                 665                 670

Trp Gly Ser Asn Val Gly Leu Ala Leu Met Leu Ile Met Ser Leu Phe
        675                 680                 685

Pro Ser Gly Val Leu Gln Val Trp Asp Val Val Gln His Gly Tyr Trp
    690                 695                 700

His Ala Arg Ser Leu Asp Tyr Ile Gly Ser Glu Arg Ser Arg Leu Ile
705                 710                 715                 720

Glu Trp Leu Arg Leu Pro Gly Asp Leu Val Phe Ile Leu Phe Gly Ala
            725                 730                 735

Ile Pro Leu Ala Ile Ala Ser Ile Lys Gly Trp Leu Asp Val His
        740                 745                 750

<210> SEQ ID NO 21
<211> LENGTH: 1581
<212> TYPE: DNA
<213> ORGANISM: Methylomonas 16a
<220> FEATURE:
```

<223> OTHER INFORMATION: ORF11
<220> FEATURE:
<223> OTHER INFORMATION: nirS gene

<400> SEQUENCE: 21

| | |
|---|---|
| atgatgaaaa caacaactaa aagacgactg aatcaatccc ttctggcgag tgctatcgcc | 60 |
| gcgttactgt cgtccggtgc ggtgctggcg aaatccgaca gcccacacga catctacatg | 120 |
| gataattgcg ccagctgcca cggcgcggat cacggtggct atctggcgcc agccttgaat | 180 |
| gccgatacct tgaaaggtcg tagccctacg gcgttgcgta ccatcgtcat ggccggcagc | 240 |
| ttcgatacgc tgatgcctcc cttctacggc aaactgagcg acgacgagat cgcggcgtg | 300 |
| atcaagcatt tgcaggaaac cccgaaacag ccgaatccgg cctggaccat cgacgacatg | 360 |
| aagaagtcct tgaaggttta cgtcaaggat gagagcaccc tgcctggcaa gccgactttc | 420 |
| caaatcgata acatcgataa tctgatcggc gtggcggcac gcggcaaata cggccgtggc | 480 |
| gaaggctcca aagctatttt catcaacagc accaaccatc aaaaagtcgg cgaagtggct | 540 |
| accggcaccg ccgcgcatat catcgacttc aatcctgcca cccgcgctg ggcttacgta | 600 |
| aaaaccgaca ccgccgagat tttcaaggta gatttgtatt cgatgcaggc ggtccgcagc | 660 |
| atcaagacag gttacaacgg ccccggcatg ggggtatccc gcgacggcaa atacatcatg | 720 |
| gccggctcct tcgtgccgca taacgccgta atcctggatg ccgaaaccct ggaaccgttg | 780 |
| aaaaccttcg aactggaagg catcgatccc gacggtaaac atgtttcttc cgactcgggc | 840 |
| atgatcatcg taccccttta tgccgacgtg ttcgcgattg cgctggaaaa tgccggccag | 900 |
| gtctggatcg tcgattacaa caaagaaggc ttcccggtca ccaaaatcga aaagtgggc | 960 |
| cgtcacttgc acgacgcctt cctgacgcat ggcggcaaga aactgatggt ggcgtcttat | 1020 |
| gacgacagca tcgtcgccgc gatcgatctg gaaaaacgcg aactgatcaa gcaattgcca | 1080 |
| gcgggttgtg tgccgcacgt cggtggcggc gcggcggtcg tggttgatgg tcgtaccttg | 1140 |
| ggcttcggta ccaactttgg cgattgcgac aagatggtcg tcagcgtttg ggatttggac | 1200 |
| aaaatggaag tcgtcaaaca agtaccggtt tcaggtggca ctgaatcgcc tgcggctcat | 1260 |
| gccaacgcac cttatgtcgc ggttgacatc atcagcaaag acagacgtgc acgcaccatt | 1320 |
| cagttgatcg acaagaaaac cctggaagtt gccaaaactc tggatgtcgg cggccacgcc | 1380 |
| tacttcccgg aatatagcgc cgacggcaaa ttcctctatg tcagtgccgg ctacaatggc | 1440 |
| gacgaagtcg tggtttacga ttccaatacc ttgcaaaaag tggcgaccgt gccgatggaa | 1500 |
| agtcctgctg gtatcttctc cagaggccgt gtcaaataca tgactcgcgg tctgtcacct | 1560 |
| gacgaaatgg agcaaggcaa a | 1581 |

<210> SEQ ID NO 22
<211> LENGTH: 527
<212> TYPE: PRT
<213> ORGANISM: Methylomonas 16a
<220> FEATURE:
<223> OTHER INFORMATION: NirS

<400> SEQUENCE: 22

Met Met Lys Thr Thr Thr Lys Arg Arg Leu Asn Gln Ser Leu Leu Ala
 1               5                  10                  15

Ser Ala Ile Ala Ala Leu Leu Ser Ser Gly Ala Val Leu Ala Lys Ser
            20                  25                  30

Asp Ser Pro His Asp Ile Tyr Met Asp Asn Cys Ala Ser Cys His Gly
        35                  40                  45

-continued

```
Ala Asp His Gly Gly Tyr Leu Ala Pro Ala Leu Asn Ala Asp Thr Leu
 50                  55                  60

Lys Gly Arg Ser Pro Thr Ala Leu Arg Thr Ile Val Met Ala Gly Ser
 65                  70                  75                  80

Phe Asp Thr Leu Met Pro Pro Phe Tyr Gly Lys Leu Ser Asp Asp Glu
                 85                  90                  95

Ile Arg Gly Val Ile Lys His Leu Gln Glu Thr Pro Lys Gln Pro Asn
            100                 105                 110

Pro Ala Trp Thr Ile Asp Met Lys Lys Ser Leu Lys Val Tyr Val
            115                 120                 125

Lys Asp Glu Ser Thr Leu Pro Gly Lys Pro Thr Phe Gln Ile Asp Asn
130                 135                 140

Ile Asp Asn Leu Ile Gly Val Ala Ala Arg Gly Lys Tyr Gly Arg Gly
145                 150                 155                 160

Glu Gly Ser Lys Ala Ile Phe Ile Asn Ser Thr Asn His Gln Lys Val
                165                 170                 175

Gly Glu Val Ala Thr Gly Thr Ala Ala His Ile Ile Asp Phe Asn Pro
            180                 185                 190

Ala Asn Pro Arg Trp Ala Tyr Val Lys Thr Asp Thr Ala Glu Ile Phe
            195                 200                 205

Lys Val Asp Leu Tyr Ser Met Gln Ala Val Arg Ser Ile Lys Thr Gly
210                 215                 220

Tyr Asn Gly Pro Gly Met Gly Val Ser Arg Asp Gly Lys Tyr Ile Met
225                 230                 235                 240

Ala Gly Ser Phe Val Pro His Asn Ala Val Ile Leu Asp Ala Glu Thr
                245                 250                 255

Leu Glu Pro Leu Lys Thr Phe Glu Leu Glu Gly Ile Asp Pro Asp Gly
            260                 265                 270

Lys His Val Ser Ser Asp Ser Gly Met Ile Ile Gly Thr Pro Tyr Ala
            275                 280                 285

Asp Val Phe Ala Ile Ala Leu Glu Asn Ala Gly Gln Val Trp Ile Val
290                 295                 300

Asp Tyr Asn Lys Glu Gly Phe Pro Val Thr Lys Ile Glu Lys Val Gly
305                 310                 315                 320

Arg His Leu His Asp Ala Phe Leu Thr His Gly Gly Lys Lys Leu Met
                325                 330                 335

Val Ala Ser Tyr Asp Asp Ser Ile Val Ala Ile Asp Leu Glu Lys
            340                 345                 350

Arg Glu Leu Ile Lys Gln Leu Pro Ala Gly Cys Val Pro His Val Gly
            355                 360                 365

Gly Gly Ala Ala Val Val Asp Gly Arg Thr Leu Gly Phe Gly Thr
370                 375                 380

Asn Phe Gly Asp Cys Asp Lys Met Val Val Ser Val Trp Asp Leu Asp
385                 390                 395                 400

Lys Met Glu Val Val Lys Gln Val Pro Val Ser Gly Thr Glu Ser
                405                 410                 415

Pro Ala Ala His Ala Asn Ala Pro Tyr Val Ala Val Asp Ile Ile Ser
            420                 425                 430

Lys Asp Arg Arg Ala Arg Thr Ile Gln Leu Ile Asp Lys Lys Thr Leu
            435                 440                 445

Glu Val Ala Lys Thr Leu Asp Val Gly His Ala Tyr Phe Pro Glu
450                 455                 460

Tyr Ser Ala Asp Gly Lys Phe Leu Tyr Val Ser Ala Gly Tyr Asn Gly
```

-continued

```
465                 470                 475                 480

Asp Glu Val Val Val Tyr Asp Ser Asn Thr Leu Gln Lys Val Ala Thr
            485                 490                 495

Val Pro Met Glu Ser Pro Ala Gly Ile Phe Ser Arg Gly Arg Val Lys
            500                 505                 510

Tyr Met Thr Arg Gly Leu Ser Pro Asp Glu Met Glu Gln Gly Lys
            515                 520                 525
```

GENES ENCODING DENITRIFICATION ENZYMES

This application claims the benefit of U.S. Provisional Application No. 60/185,621 filed Feb. 29, 2000.

FIELD OF THE INVENTION

This invention is in the field of microbial denitrification. More specifically, this invention pertains to nucleic acid fragments encoding enzymes useful for microbial denitrification.

BACKGROUND OF THE INVENTION

The complete pathway for microbial denitrification has been established as:

$$NO_3 \rightarrow NO_2 \rightarrow NO \rightarrow N_2O \rightarrow N_2$$

(Ye et al., *Appl. Environ. Microbiol.* 60:1053–1058 (1994); Zumft et al., *Microbiol. Mol. Biol. Rev.* 61:533–616 (1997)). In bacterial denitrification, NO is produced from $NO_3$—in two consecutive reactions catalyzed by the two metalloenzymes nitrate reductase and nitrite reductase, and then is decomposed into $N_2O$ by nitric oxide reductase. These quintessential enzymes catalyze the conversion of a mineral form of nitrogen to a gaseous form. It is well recognized that gaseous forms of nitrogen compounds are no longer easily available for assimilation by the biomass.

Many aerobic organisms have the ability to utilize nitrate or nitrite as the terminal electron acceptor, in the absence of oxygen, and thus grow anaerobically via a process known as nitrate respiration. Nitrate respiration yields energy which can be used for cellular growth and/or production of cellular products (Gottschalk, G. *Bacterial Metabolism* p 122–126 Springer-Verlag (1985)).

Microbial denitrification is catalyzed by a series of enzyme-catalyzed reactions which together reductively convert nitrate to gaseous dinitrogen. In the natural environment, denitrification plays a major role in completing the nitrogen cycle by converting nitrate or nitrite to nitrogen gas. In the denitrification process, the bacteria use nitrate, rather than oxygen, as the ultimate electron acceptor in the series of reactions to generate a transmembrane proton gradient that is used to synthesize ATP. These nitrogenous reactants and products chemically define, the scope of the process under consideration (Gottschalk, G., *Bacterial Metabolism*, p 122–126 Springer-Verlag (1985); Zumft, W. G., *Microbiology and Molecular Biology Reviews*, 61:533–616 (1997); Zumft, W. G., *The Prokaryotes* Vol. 1 p 554–582 Springer-Verlag (1992)). Ecologically, the result of these processes is removal of nitrogen from soils (Zumft, W. G., *The Denitrifying Prokaryotes*. In: *The Prokaryotes* Vol. 1 p 554–582 Springer-Verlag (1992)).

In practical applications, microbial denitrification has been widely used for water purification (Mateju et al., *Enzyme Microb. Technol.* 14:172–183 (1992)). However, nitrous oxide ($N_2O$) has been shown to have detrimental effect on the stratospheric ozone layer (de Boer et al., *Eur. J. Biochem.* 242:592–600 (1996)). NOx, along with carbon monoxide and hydrocarbons can lead to an increase in the amount of stratospheric ozone. Thus, the production of $N_2O$ and nitric oxide (NO) due to incomplete denitrification is of concern. It will be useful therefore to devise new and better methods for denitrification of industrial waste streams to effect complete denitrification. The identification of genes encoding proteins responsible for key denitrification reactions will be essential for the development of improved denitrification methods.

Genes encoding enzymes useful in denitrification are known. For example Palmedo et al., [*Eur. J Biochem.* 232 (3), 737–746 (1995)] and Kawasaki et al., [*J. Bacteriol.* 179 (1), 235–242 (1997)] teach the isolation of *nir* genes from *Pseudomonas*, encoding nitrite reductase. Similarly, Lin et al., [*J. Bacteriol.* 175:2370–2378 (1993)] report the cloning of *nasA* and *nasB* genes from *Klebsiella*, which encode enzymes involved in assimilatory nitrate and nitrite reductase, respiration. Additionally Zumft et al., [*Eur. J Biochem.* 219:481–490 (1994)] and Glockner et al., [*Biochim. Biophys. Acta* 1277 (1–2), 6–12 (1996)]teach the isolation of the structural genes for the nitric oxide reductase complex, *norC* and *norB*, from *Pseudomonas stutzeri*, and Cramm et al., [*J. Bacteriol.* 179 (21), 6769–6777 (1997)] discuss the isolation of the *norZ* gene.

Although genes involved in denitrification are well characterized, all have been isolated from a tightly focused group of genera, for example, *Pseudomonas, Klebsiella, Rhodobacter, Rhodococcus, Paracoccus,* and other bacteria typically associated with soil and groundwater detoxification processes. The presence of genes involved in denitrification in other species is rare. In spite of this, Applicants have isolated a number of unique open reading frames encoding denitrifying enzymes from a *Methylomonas* sp. The literature suggests that obligate methanotrophic bacteria including *Methylomonas* 16a belong to the group of nitrifying bacteria (Hanson and Hanson, *The Methanotrophic Bacteria. Microbiol. Rev.* 60:439–471 (1996)). This is due to the ability of these organisms to oxygenate ammonia to form hydroxylamine (ammonia monooxygenase reaction) which is analogous to the methane monooxygenase reaction to form methanol. The hydroxylamine is then further oxidized to nitrite. Nitrite oxidation to nitrate can occur enzymatically or spontaneously in air via chemical oxidation. Growth of methanotrophs on nitrate as the sole nitrogen source for biosynthesis, in place of ammonia is also well known (Lidstrom, L.E., *The aerobic methylotrophic bacteria. The Prokaryotes,* Springer-Verlag, p 431–445 (1992)). However, denitrification processes in methanotrophs has not been reported. The literature further indicates that methanotrophic bacteria are capable of reactions such as nitrate assimilation and nitrification but the nitrate respiration (denitrification) process has not been found in the obligate methanotrophs on a large or significant scale.

The problem to be solved, therefore, is to provide new genes and enzymes useful for performing denitrification reactions.

Applicants have solved the stated problem by isolating a gene cluster containing 11 open reading frames (ORFs) encoding enzymes involved in microbial denitrification. These genes were isolated from an obligate methanotroph, heretofore not recognized as having a denitrifying pathway.

SUMMARY OF THE INVENTION

The present invention provides an isolated nucleic acid fragment encoding a bacterial nitrite reductase selected from the group consisting of: (a) an isolated nucleic acid fragment encoding the amino acid sequence selected from the group consisting of SEQ ID NOs:2, 4, 6, 8, 10, 12 and 22; (b) an isolated nucleic acid fragment encoding a polypeptide of at least 147 amino acids having at least 49% identity based on the Smith-Waterman method of alignment with the amino acid sequence selected from the group consisting of SEQ ID NOs:2, 4, 6, 8, 10, 12 and 22; (c) an isolated nucleic acid fragment that hybridizes with (a) under the following hybridization conditions: (0.1 X SSC, 0.1% SDS, 65° C. and washed with 2 X SSC, 0.1% SDS followed by 0.1 X SSC, 0.1% SDS); and (d) an isolated nucleic acid fragment that is complementary to (a), (b), or (c).

In an alternate embodiment the present invention provides an isolated nucleic acid fragment encoding a bacterial nitric oxide reductase selected from the group consisting of: (a) an isolated nucleic acid fragment encoding the amino acid sequence selected from the group consisting of SEQ ID NOs:16, 18 and 20; (b) an isolated nucleic acid fragment encoding a polypeptide of at least 214 amino acids having at least 39% identity based on the Smith-Waterman method of alignment with the amino acid sequence selected from the group consisting of SEQ ID NOs:16, 18, and 20; (c) an isolated nucleic acid fragment that hybridizes with (a) under the following hybridization conditions: (0.1 X SSC, 0.1% SDS, 65° C. and washed with 2 X SSC, 0.1% SDS followed by 0.1 X SSC, 0.1% SDS); and (d) an isolated nucleic acid fragment that is complementary to (a), (b), or (c).

In another embodiment the present invention provides an isolated nucleic acid fragment encoding a bacterial nitrate reductase selected from the group consisting of: (a) an isolated nucleic acid fragment encoding the amino acid sequence as set forth in SEQ ID NO:14; (b) an isolated nucleic acid fragment encoding a polypeptide of at least 920 amino acids having at least 51% identity based on the Smith-Waterman method of alignment with the amino acid sequence as set forth in SEQ ID NO:14; (c) an isolated nucleic acid fragment that hybridizes with (a) under the following hybridization conditions: (0.1 X SSC, 0.1% SDS, 65° C. and washed with 2 X SSC, 0.1% SDS followed by 0.1 X SSC, 0.1% SDS); and (d) an isolated nucleic acid fragment that is complementary to (a), (b), or (c).

The invention further provides polypeptides encoded by the instant bacterial denitrifying sequences.

Additionally the invention provides chimeric genes comprising the instant genes operably linked to suitable regulatory sequences.

In another embodiment the invention provides a transformed host cell comprising the instant chimera. Preferred host cells comprise bacteria, yeast, and filamentous fungi.

In an alternate embodiment the present invention provides a method of obtaining a nucleic acid fragment encoding all or a substantial portion of the instant bacterial denitrifying sequences comprising: (a) probing a genomic library with the nucleic acid fragment encoding the instant denitrifying enzymes; (b) identifying a DNA clone that hybridizes with the nucleic acid fragment of step (a); (c) sequencing the genomic fragment that comprises the clone identified in step (b), wherein the sequenced genomic fragment encodes all or substantially all of the amino acid sequence encoding the instant bacterial denitrifying enzymes.

In similar fashion the present invention provides a method of obtaining a nucleic acid fragment encoding all or a substantial portion of the instant bacterial denitrifying enzymes comprising: (a) synthesizing at least one oligonucleotide primer corresponding to a portion of the sequences encoding the instant bacterial denitrifying enzymes; and (b) amplifying an insert present in a cloning vector using the oligonucleotide primer of step (a); wherein the amplified insert encodes a portion of an amino acid sequence encoding the instant bacterial denitrifying enzymes.

The present invention additionally provides products produced by the above methods.

In a preferred embodiment the invention provides a method for reduction of nitrite, nitrate or nitric oxide comprising: (a) transforming a host cell with a chimeric gene comprising a nucleic acid fragment encoding the instant bacterial denitrifying enzymes, the chimeric gene operably linked to at least one suitable regulatory sequence; (b) growing the transformed host cell of step (a) in the presence of an effective amount of nitrite and under conditions wherein said chimeric gene is expressed and where said nitrite, nitrate or nitric oxide is reduced.

In an alternate embodiment the invention provides a mutated bacterial denitrifying gene encoding a protein having an altered biological activity produced by a method comprising the steps of:

(i) digesting a mixture of nucleotide sequences with restriction endonucleases wherein said mixture comprises:
  a) a native bacterial denitrifying sequence;
  b) a first population of nucleotide fragments which will hybridize to said native bacterial sequence;
  c) a second population of nucleotide fragments which will not hybridize to said native bacterial denitrifying sequence; wherein a mixture of restriction fragments are produced;
(ii) denaturing said mixture of restriction fragments;
(iii) incubating the denatured said mixture of restriction fragments of step (ii) with a polymerase;
(iv) repeating steps (ii) and (iii) wherein a mutated bacterial denitrifying sequence is produced encoding a protein having an altered biological activity.

BRIEF DESCRIPTION OF THE DRAWINGS AND SEQUENCE DESCRIPTIONS

FIG. 1 is a plot showing the reduction of NO2 and NO3 by *Methylomonas* 16a.

Figure 1A:
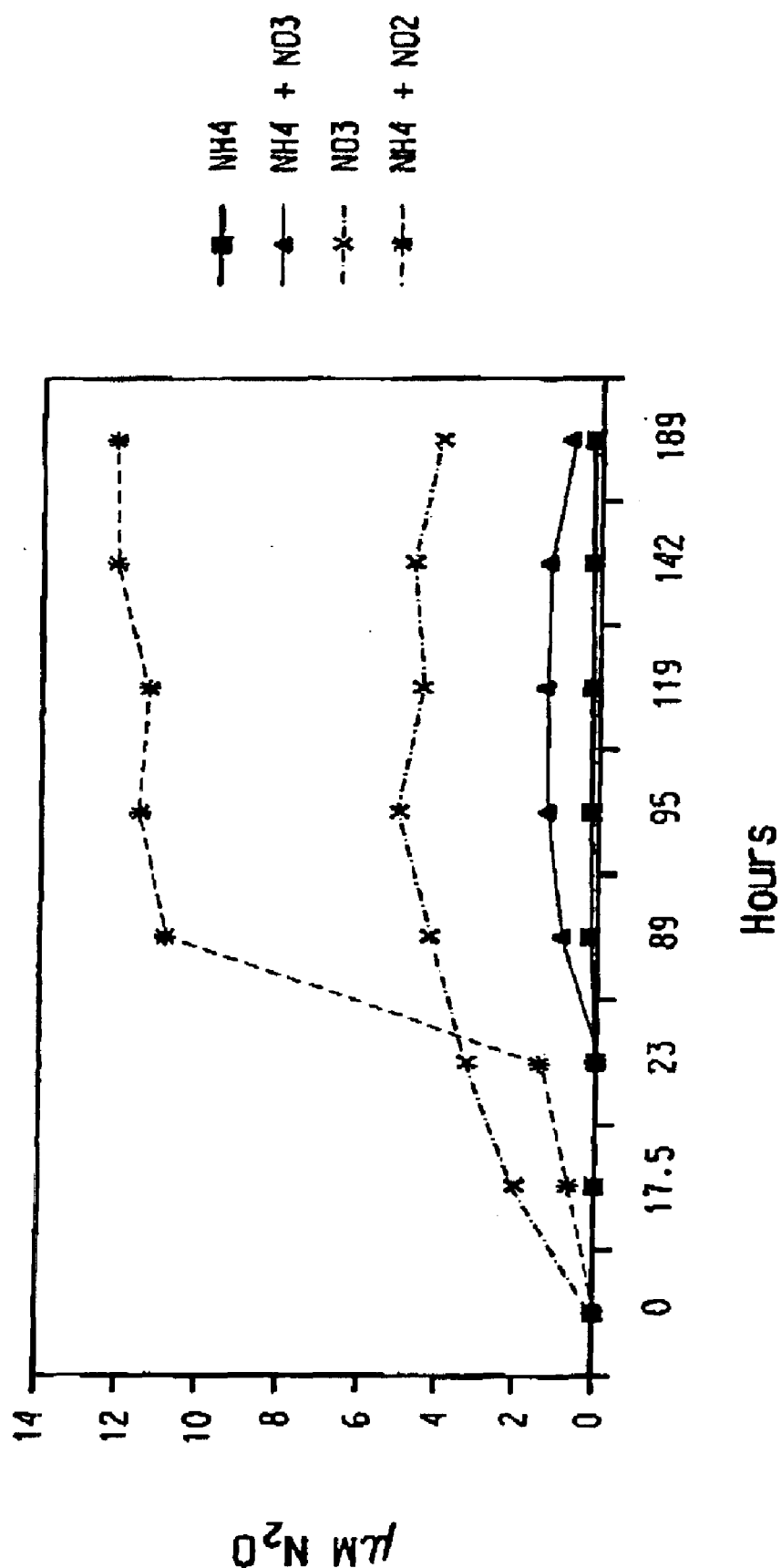

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of ORF1 encoding *nirF* gene.

SEQ ID NO:2 is the deduced amino acid sequence of *nirF* encoded by ORF1.

SEQ ID NO:3 is the nucleotide sequence of ORF2 encoding *nirD* gene.

SEQ ID NO:4 is the deduced amino acid sequence of *nirD* encoded by ORF2.

SEQ ID NO:5 is the nucleotide sequence of ORF3 encoding *nirL* gene.

SEQ ID NO:6 is the deduced amino acid sequence of nirL gene encoded by ORF3.

SEQ ID NO:7 is the nucleotide sequence of ORF4 encoding nirG gene.

SEQ ID NO:8 is the deduced amino acid sequence of nirG encoded by ORF4.

SEQ ID NO:9 is the nucleotide sequence of ORF5 encoding nirH gene.

SEQ ID NO:10 is the deduced amino acid sequence of nirH encoded by ORF5.

SEQ ID NO:11 is the nucleotide sequence of ORF6 encoding nirJ gene.

SEQ ID NO:12 is the deduced amino acid sequence of nirJ encoded by ORF6.

SEQ ID NO:13 is the nucleotide sequence of ORF7 encoding nasA gene.

SEQ ID NO:14 is the deduced amino acid sequence of nasA gene encoded by ORF7.

SEQ ID NO:15 is the nucleotide sequence of ORF8 encoding norC gene.

SEQ ID NO:16 is the deduced amino acid sequence of norC encoded by ORF8.

SEQ ID NO:17 is the nucleotide sequence of ORF9 encoding norB gene.

SEQ ID NO:18 is the deduced amino acid sequence of norB encoded by ORF9.

SEQ ID NO:19 is the nucleotide sequence of ORF10 encoding norZ gene.

SEQ ID NO:20 is the deduced amino acid sequence of norZ encoded by ORF10.

SEQ ID NO:21 is the nucleotide sequence of ORF11 encoding nirS gene.

SEQ ID NO:22 is the deduced amino acid sequence of nirS encoded by ORF11.

DETAILED DESCRIPTION OF THE INVENTION

The genes and their expression products are useful for the creation of recombinant organisms that have the ability to denitrify toxic waste substances, for the identification of new denitrifying species of bacteria and for fermentation processes in the absence or presence of oxygen. Nucleic acid fragments encoding at least a portion of several of the above mentioned enzymes have been isolated from a strain of Methylomonas 16a and identified by comparison to public databases containing nucleotide and protein sequences using the BLAST and FASTA algorithms well known to those skilled in the art.

The genes and gene products of the present invention may be used in a variety of ways for the further reduction of nitrite to nitrous oxide. The activity of the present genes and gene products has been confirmed by studies showing the denitrifying activity of the source strain, Methylomonas 16a.

The genes for denitrification may be used to remove soluble nitrates from waters or processes where nitrates or other oxygenated nitrogen derivatives are problematic. Microbial denitrification removes nitrates from soils via formation of nitrous oxide or dinitrogen. This is a normal part of the global nitrogen cycle. Where nitrites occur at toxic or problematic levels in ground or wastewater, this is often due to the activity of nitrifying bacteria (including many methanotrophs) that convert the ammonia released by decomposing proteinaceous waste to nitrite. Addition of inexpensive carbon substrates such as methane or methanol and methanotrophic bacteria containing the present genes for denitrification, allows for the cost-effective removal of the nitrite to nitrous oxide.

In this disclosure, a number of terms and abbreviations are used. The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "bacterial denitrifying gene" or "bacterial denitrifying sequence" refers to the sequences of the present application isolated from Methylomonas 16a and encoding enzymes having the ability to reduce nitrite, nitrate or nitric oxide. Bacterial denitrifying sequences comprise ORF's 1–11 as discussed in the present application.

The term "bacterial denitrifying enzyme" refers to the enzymes encoded by sequences of the present application isolated from Methylomonas 16a which have the ability to reduce nitrite, nitrate or nitric oxide. Bacterial denitrifying enzymes comprise those enzymes encoded by ORF's 1–11 as discussed in the present application.

The term "denitrification" or "nitrate respiration" refers to the microbial process of the reduction of nitrate or nitrite to gaseous end products such as nitrous oxide, nitric oxide or dinitrogen. In the process of carrying out these reductions the cells derive useful biological energy hence the term nitrate respiration.

The term "nir" refers to nitrite reductase enzyme encoded by ORF1, 2, 3, 4, 5, 6, and 11. The nitrite reductase catalyzes the reduction of nitrite ($NO_2$) to nitric oxide (NO). There are several enzymes in the nitrite reductase family. They are further identified as nirD, nirF, nirG, nirH, nirJ, nirL and nirS.

The term "nasA" refers to nitrate reductase enzyme encoded by ORF7 and catalyzes the reduction of nitrate ($NO_3$) to nitrite($NO_2$).

The term "nor" refers to nitric oxide reductase enzyme encoded by ORF8, 9, and 10. The nitric oxide reductase catalyzes the reduction of nitric oxide(NO) to nitrous oxide ($N_2O$). There are several enzymes in the nitric oxide reductase family. They are further identified as norB, norC or norZ.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:
1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1 X SSC, 0.1% SDS, 65° C. and washed with 2 X SSC, 0.1% SDS followed by 0.1 X SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5 X SSC, 0.1% SDS, 0.25% milk, and no formamide; or 30% formamide, 5 X SSC, 0.5% SDS. Moderate stringency hybridization conditions correspond to a higher Tm, e.g., 40% formamide, with 5 X or 6 X SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer- automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data. Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, BLASTX (Altschul et al., *J. Mol. Biol.* 215:403–410 (1990)), and FASTA, version 3.2, Dec. 1998, (Pearson et al., *Proc. Natl. Acad. Sci. U.S.A.* 85:2444–2448 (1988), and Pearson, *Meth. In Molecular Biology* 132:185–219 (1999)). In the FASTA package the final pairwise alignments are generated using ssearch3, an implementation of the Smith-Waterman algorithm (Smith, Waterman *J Mol. Biol.* 147:195–197(1981)) The BLAST programs are publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J Mol. Biol.* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1, it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID Nos. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene"refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (MRNA) or antisense RNA derived from the nucleic acid fragment of the invention. Expression may also refer to translation of MRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press 30 Spring Harbor, N.Y. (1984); and by Ausubel, F. M. et al., *Current Protocols in Molecular Biology*, published by Greene Publishing Assoc. and Wiley-Interscience (1987).

A variety of nucleotide sequences have been isolated from *Methylomonas* 16a encoding gene products involved in denitrification reactions. ORF's1–6 and 11 for example encode nitrite reductase (Nir) enzymes, ORF7 encodes a nitrate reductase (Nas) and ORF's8–10 encode nitric oxide reductase enzymes (Nor).

Comparison of the Nir base and deduced amino acid sequences to public databases reveals that the most similar known sequences range from a distant as about 28% identical at the amino acid level over a length of 527 amino acids (ORF11, NirS) to about 59% identical over a length of 390 amino acids (ORF1, NirF) using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Accordingly preferred polypeptides of the instant invention are those active proteins which are at least 49% identical to the amino acid sequence of reported herein over a length of 147 amino acids. More preferred amino acid fragments are at least about 80%–90% identical to the sequences herein. Most preferred are nucleic acid fragments that are at least 95% identical to the amino acid fragments reported herein. Similarly, preferred Nir encoding nucleic acid sequences corresponding to the instant ORF's are those encoding active proteins and which are at least 80% identical to the nucleic acid sequences of reported herein. More preferred Nir nucleic acid fragments are at least 90% identical to the sequences herein. Most preferred are Nir nucleic acid fragments that are at least 95% identical to the nucleic acid fragments reported herein.

Comparison of the a nitrate reductase (Nas) base and deduced amino acid sequence to public databases reveals that the most similar known sequence is 51% identical at the amino acid level over a length of 920 amino acids (ORF7, NasA) using a Smith-Waterman alignment algorithm (W.R. Pearson supra). More preferred amino acid fragments are at least about 80%–90% identical to the sequences herein. Most preferred are nucleic acid fragments that are at least 95% identical to the amino acid fragments reported herein. Similarly, preferred NasA encoding nucleic acid sequences corresponding to the instant ORF's are those encoding active proteins and which are at least 80% identical to the nucleic acid sequences of reported herein. More preferred NasA nucleic acid fragments are at least 90% identical to the sequences herein. Most preferred are NasA nucleic acid fragments that are at least 95% identical to the nucleic acid fragments reported herein.

Similarly comparison of the Nor base and deduced amino acid sequences to public databases reveals that the most similar known sequences range from a distant as about 32% identical at the amino acid level over a length of 214 amino acids (ORF8, NorC) to about 39% identical over a length of 751 amino acids (ORF10, NorZ) using a Smith-Waterman alignment algorithm (W. R. Pearson supra). Accordingly preferred polypeptides of the instant invention are those active proteins which are at least 39% identical to the amino acid sequence of reported herein over a length of 214 amino acids. More preferred amino acid fragments are at least about 80%–90% identical to the sequences herein. Most preferred are nucleic acid fragments that are at least 95% identical to the amino acid fragments reported herein. Similarly, preferred Nor encoding nucleic acid sequences corresponding to the instant ORF's are those encoding active proteins and which are at least 80% identical to the nucleic acid sequences of reported herein. More preferred Nor nucleic acid fragments are at least 90% identical to the sequences herein. Most preferred are Nor nucleic acid fragments that are at least 95% identical to the nucleic acid fragments reported herein.

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad Sci.* USA 82, 1074, (1985)) or strand displacement amplification (SDA, Walker, et al., *Proc. Natl. Acad. Sci. U.S.A.*, 89, 392, (1992)).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1(1984); Maniatis).

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host for the synthesis of new products heretofore not possible using the host. Additionally the gene products may be useful for conferring higher growth yields on the host or for enabling alternative growth mode to be utilized.

Preferred heterologous host cells for express of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because transcription, translation and the protein biosynthetic apparatus is the same irrespective of the cellular feedstock, functional genes are expressed irrespective of carbon feedstock used to generate cellular biomass. Large scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include but are not limited to fungal or yeast species such as *Aspergillus, Trichoderma, Saccharomyces, Pichia, Candida, Hansenula,* or bacterial species such as *Salmonella, Bacillus, Acinetobacter, Rhodococcus, Streptomyces, Escherichia, Pseudomonas, Methylomonas, Methylobacter, Methylococcus, Methylosinus, Methylomicrobium, Methylocystis, Alcaligenes; Synechocystis, Anabaena, Thiobacillus, Methanobacterium* and *Klebsiella*.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the enzymes and alter the metabolism of the host.

For example, denitrifying genes are used in at least two different processes in nature, nitrate respiration, and nitrate assimilation. Nitrate respiration is the denitrification process by which bacteria utilize nitrate as opposed to oxygen as the final electron acceptor to synthesize ATP. The pathways and intermediates are shown below in Table 1 together with the enzyme names and gene designations in the denitrification pathway.

TABLE 1

Denitrification

| Reactant | Products | Enzyme | Gene |
|---|---|---|---|
| $NO_3$ | $NO_2$ | Respiratory nitrate reductase | Nar/Nas |
| $NO_2$ | NO | Respiratory nitrite reductase | Nir |
| NO | $N_2O$ | Nitric oxide reductase | Nor |
| $N_2O$ | $N_2$ | Nitrous oxide reductase | Nos |

In nitrate assimilation, the nitrate ion serves as a source of nitrogen, in place of ammonium ion, for the production of nitrogen-containing cellular constituents such as amino acids and protein (Table 2) (Zumft, W.G., *Microbiology and Molecular Biology Reviews*, 61:533–616 (1997)). Nitrate assimilation utilizes NADPH (pyridine cofactor) linked reductases whereas the respiratory process utilizes cytochrome as electron donors. Nitrate assimilation results in ammonium formation whereas respiration generates dinitrogen as end product (Gottschalk, G., *Bacterial Metabolism*, p 122–126 Springer-Verlag (1985)).

TABLE 2

Nitrate Assimilation

| Reactant | Products | Enzyme |
|---|---|---|
| $NO_3$ | $NO_2$ | NADPH-linked nitrate reductase |
| $NO_2$ | $NH_4$ | NADPH-linked nitrite reductase |

Accordingly it is expected, for example, that introduction of chimeric gene encoding the instant bacterial reductase enzymes under the control of the appropriate promoters, will demonstrate increased denitrifying activity. It is contemplated that it will be useful to express the instant genes both in host cells having preexisting denitrifying pathways as well as those hosts lacking such pathways. Introduction of the present reductase genes into denitrifying bacteria (such as *Paracoccus denitrificans, Rhodobacter sphaeroides, Thiosphaera pantotropha* and various *Pseudomonas* sp.) will result in elevated levels of reductase activity improving the rate of denitrification. Additionally, the instant genes may also be introduced into non-denitrifying bacteria where there are advantages to convey denitrifying properties to a non-denitrifying organism. Non denitrifying bacteria suitable in the present invention include but are not limited to *Salmonella, Bacillus, Acinetobacter, Rhodococcus, Streptomyces,* and *Escherichia*. It is also expected, for example, that introduction of chimeric genes encoding one or more of the instant sequences can help overcome or partially overcome oxygen requirement by substituting nitrate, nitrite, nitric oxide or nitrous oxide in place of oxygen as an electron acceptor in an obligate aerobe production system.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TP1 (useful for expression in *Saccharomyces*); AOX1 (useful for expression in *Pichia*); and *lac, ara, tet, trp, $IP_L$, $IP_R$,* T7, *tac,* and *trc* (useful for expression in *Escherichia coli*) as well as the *amy, apr, npr* promoters and various phage promoters useful for expression in *Bacillus*.

Termination control regions may also be derived from various genes native to the preferred hosts. Optionally, a termination site may be unnecessary, however, it is most preferred if included.

It is contemplated that the present nucleotides may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling"(U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Manatis supra).

Furthermore, a hybrid protein can be assembled by fusion of functional domains using the gene shuffling (exon shuffling) method (Nixon et al., PNAS, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

Many external changes such as changes in growth condition, exposure to chemicals etc.. can cause induction or repression of genes in the cell. The induction or repression of gene can be used for a screening system to determine the best growth condition for a production organism, or for drug discovery with similar mode of action compound, to mention a few. On the other hand, by amplifying or disrupting genes, one can manipulate the production of the amount of cellular products as well as the timeline. All or portion of the nucleic acid fragments of the instant invention may also be used as probes for gene expression monitoring and gene expression profiling. All nir genes may be monitored for expression and or regulation of expression by oxygen. It may be desirable to deregulate or derepress these genes by knocking out regulatory elements or over-expressing regulatory elements.

For example, all or a portion of the instant nucleic acid fragments may be immobilized on a nylon membrane or a glass slide. A Generation II DNA spotter (Molecular Dynamics) is one of the available technology to array the DNA samples onto the coated glass slides. Other array methods are also available and well known in the art. After the cells were grown in various growth conditions or treated with potential candidates, cellular RNA is purified. Fluorescent or radioactive labeled target cDNA can be made by reverse transcription of mRNA. The target mixture is hybridized to the probes and washed using conditions well known in the art. The amount of the target gene expression is quantified by the intensity of radioactivity or fluorescence label (e.g., confocal laser microscope: Molecular Dynamics). The intensities of radioactivity or fluorescent label at the immobilized probes are measured using the technology well known in the art. The two color fluorescence detection scheme (e.g., Cy3 and Cy5) has the advantage over radioactively labeled targets of allowing rapid and simultaneous differential expression analysis of independent samples. In addition, the use of ratio measurements compensates for probe to probe variation of intensity due to DNA concentration and hybridization efficiency. In the case of fluorescence labeling, the two fluorescent images obtained with the appropriate excitation and emission filters constitute the raw data from differential gene expression ratio values are calculated. The intensity of images are analyzed using the available software (e.g., Array Vision 4.0: Imaging Research Inc.) well known in the art and normalized to compensate for the differential efficiencies of labeling and detection of the label. There are many different ways known in the art to normalize the signals. One of the ways to normalize the signal is by correcting the signal against internal controls. Another way is to run a separate array with labeled genomic driven DNA and compare the signal with MRNA driven signals. This method also allows to measure the transcript abundance. The array data of individual gene is examined and evaluated to determine the induction or repression of the gene under the test condition.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. Molecular Cloning. A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit"programs were used the default gap creation penalty of 50 and the default gap extension penalty of 3 were used. In any case where GCG program parameters were-not prompted for, in these or any other GCG program, default values were used.

The meaning of abbreviations is as follows: "h" means hour(s), "min"means minute(s), "sec" means second(s), "d" means day(s), "mL" means milliliters, "L" means liters.

EXAMPLE 1

ISOLATION OF *METHYLOMONAS* 16A

The original environmental sample containing the isolate was obtained from pond sediment. The pond sediment was inoculated directly into growth medium with ammonium as nitrogen source under 25% methane in air. Methane was the sole source of carbon and energy. Growth was followed until the optical density at 660 nm was stable whereupon the culture was transferred to fresh medium such that a 1:100 dilution was achieved. After 3 successive transfers with methane as sole carbon and energy source the culture was plated onto growth agar with ammonium as nitrogen source and incubated under 25% methane in air. Many methanotrophic bacterial species were isolated in this manner. However, *Methylomonas* 16a was selected as the organism to study due to the rapid growth of colonies, large colony size, ability to grow on minimal media, and pink pigmentation indicative of an active biosynthetic pathway for carotenoids.

EXAMPLE 2

Preparation of Genomic DNA for Sequencing and Sequence Generation

Genomic DNA was isolated from Methylomonas according to standard protocols.

Genomic DNA and library construction were prepared according to published protocols (Friseur et al., The Minimal Gene Complement of Mycoplasma genitalium; Science 270, 1995). A cell pellet was resuspended in a solution containing 100 mM Na-EDTA pH 8.0, 10 mM Tris-HCl pH 8.0, 400 mM NaCl, and 50 mM $MgCl_2$.

Genomic DNA preparation. After resuspension, the cells were gently lysed in 10% SDS, and incubated for 30 min at 55° C. After incubation at room temperature, proteinase K was added to 100 µg/mL and incubated at 37° C. until the suspension was clear. DNA was extracted twice with Tris-equilibrated phenol and twice with chloroform. DNA was precipitated in 70% ethanol and resuspended in a solution containing 10 mM Tris-HCl and 1 mM Na-EDTA (TE) pH 7.5. The DNA solution was treated with a mix of RNAases, then extracted twice with Tris-equilibrated phenol and twice with chloroform. This was followed by precipitation in ethanol and resuspension in TE.

Library construction. 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb, or 5.0 kb) was excised, cleaned and a two-step ligation procedure was used to produce a high titer library with greater than 99% single inserts.

Sequencing. A shotgun sequencing strategy approach was adopted for the sequencing of the whole microbial genome (Fleischmann, Robert et al., Whole-Genome Random sequencing and assembly of *Haemophilus influenzae* Rd Science, 269:1995).

Sequence was generated on an ABI Automatic sequencer using dye terminator technology (U.S. 5366860; EP 272007) using a combination of vector and insert-specific primers. Sequence editing was performed in either DNAStar (DNA Star Inc., ) or the Wisconsin GCG program (Wisconsin Package Version 9.0, Genetics Computer Group (GCG), Madison, Wis.) and the CONSED package (version 7.0). All sequences represent coverage at least two times in both directions.

EXAMPLE 3

Identification and Characterization of Bacterial ORF's

ORFs encoding 1, 3, 5, 7, 9, and 11 were initially identified by conducting BLAST (Basic Local Alignment Search Tool; Altschul, S. F., et al., (1993) J Mol. Biol. 215:403–410; see also www.ncbi.nlm.nih.gov/BLAST/) searches for similarity to sequences contained in the BLAST "nr" database (comprising all non-redundant (nr) GenBank CDS translations, sequences derived from the 3-dimensional structure Brookhaven Protein Data Bank, the SWISS-PROT protein sequence database, EMBL, and DDBJ databases). The sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTP algorithm (Altschul, S. F., et al., Nucleic Acid Res. 25:3389–3402) (1997) provided by the NCBI.

All initial comparisons were done using either the BLASTNnr or BLASTPnr algorithm. A refined similarity search was performed using FASTA (version 3.2) with the default parameters settings (BLOSUM 50 scoring matrix, word size ktup=2, gap penalty=−12 for the first residue and -2 for every additional residue in the gap). The results of the FASTA comparison are given in Table 3 which summarizes the sequences to which they have the most similarity. Table 3 displays data based on the FASTA algorithm with values reported in expect values. The Expect value estimates the statistical significance of the match, specifying the number of matches, with a given score, that are expected in a search of a database of this size absolutely by chance.

Figure 2:
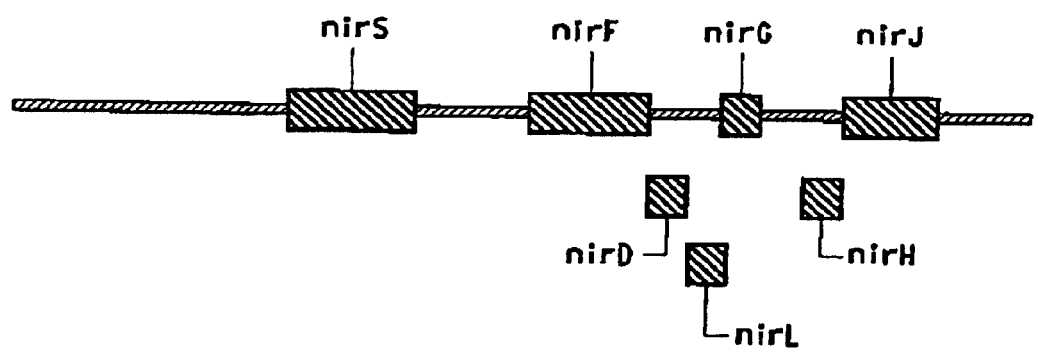
FIG. 2 shows the Nir gene cluster containing *nirS, nirF, nirD, nirL, nirG, nirH, and nirJ*, where overlapping genes (gene *nirF, nirD, nirL* and *nirG*; and genes *nirH* and *nirJ*) are shown in a different plane.
Figure 3:
FIG. 3 shows the Nor gene cluster containing norC and norB.

Gene clusters of nir genes and nor gene are shown in FIGS. 2 and 3.

TABLE 3

| ORF Name | Gene Name | Similarity Identified | SEQ ID | SEQ ID Peptide | % Identity[a] | % Similarity[b] | E-value[c] | Citation |
|---|---|---|---|---|---|---|---|---|
| ORF1 | nirF | NirF protein (*Pseudomonas*) | 1 | 2 | 59 | 85 | 1.3e-92 | Palmedo et al., Eur. J. Biochem. 232 (3), 737–746 (1995) |

TABLE 3-continued

| ORF Name | Gene Name | Similarity Identified | SEQ ID | SEQ ID Peptide | % Identity[a] | % Similarity[b] | E-value[c] | Citation |
|---|---|---|---|---|---|---|---|---|
| ORF2 | nirD | NirD protein (Pseudomonas) | 3 | 4 | 49 | 76 | 1.7e-22 | Palmedo et al., Eur. J. Biochem. 232 (3), 737–746 (1995) |
| ORF3 | nirL | NirL protein (Pseudomonas) | 5 | 6 | 49 | 73 | 6.4e-28 | Palmedo et al., Eur. J. Biochem. 232 (3), 737–746 (1995) |
| ORF4 | nirG | NirG protein (Pseudomonas) | 7 | 8 | 49 | 80 | 1.6e-25 | Kawasaki et al., J. Bacteriol. 179 (1), 235–242 (1997) |
| ORF5 | nirH | NirH protein (Pseudomonas) | 9 | 10 | 59 | 78 | 9.9e-33 | Kawasaki et al., J. Bacteriol. 179 (1), 235–242 (1997) |
| ORF6 | nirJ | NirJ protein (Pseudomonas) | 11 | 12 | 56 | 81 | 5.1e-88 | Kawasaki et al., J. Bacteriol. 179 (1), 235–242 (1997) |
| ORF7 | nasA | Nitrate reductase Klebsiella | 13 | 14 | 51 | 74 | 9.2c-123 | LIN J. T., GOLDMAN B. S., STEWART V.; J. Bacteriol. 175:2370–2378 (1993). |
| ORF8 | norC | Nitric-oxide reductase subunit C (Pseudomonas) | 15 | 16 | 32 | 70 | 1e-08 | Zumft et al., Eur. J Biochem. 219:481–490 (1994). |
| ORF9 | norB | Nitric-oxide reductase subunit B (Pseudomonas) | 17 | 18 | 39 | 70 | 3.5e-64 | Zumft et al., Eur. J Biochem. 219:481–490 (1994). |
| ORF10 | norZ | Cytochrome B subunit of nitric oxide reductase (Alcaligenes) | 19 | 20 | 39 | 69 | 1.7e-100 | Cramm, R., Siddiqui, R. A. and Friedrich, B. J. Bacteriol. 179 (21), 6769–6777 (1997). |
| ORF11 | nirS | Nitrite reductase (cytochrome cd1) (Pseudomonas) | 21 | 22 | 28 | 59 | 2.1e-25 | Glockner, A. B. and Zumft, W. G. Biochim. Biophys. Acta 1277 (1–2), 6–12 (1996) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.
% Identity, % similarity, and e-values are all reported according to FASTA analysis with Smith-Waterman computation.

EXAMPLE 4

Denitrifying Activity of *Methylomonas* 16a

Figure 1B:
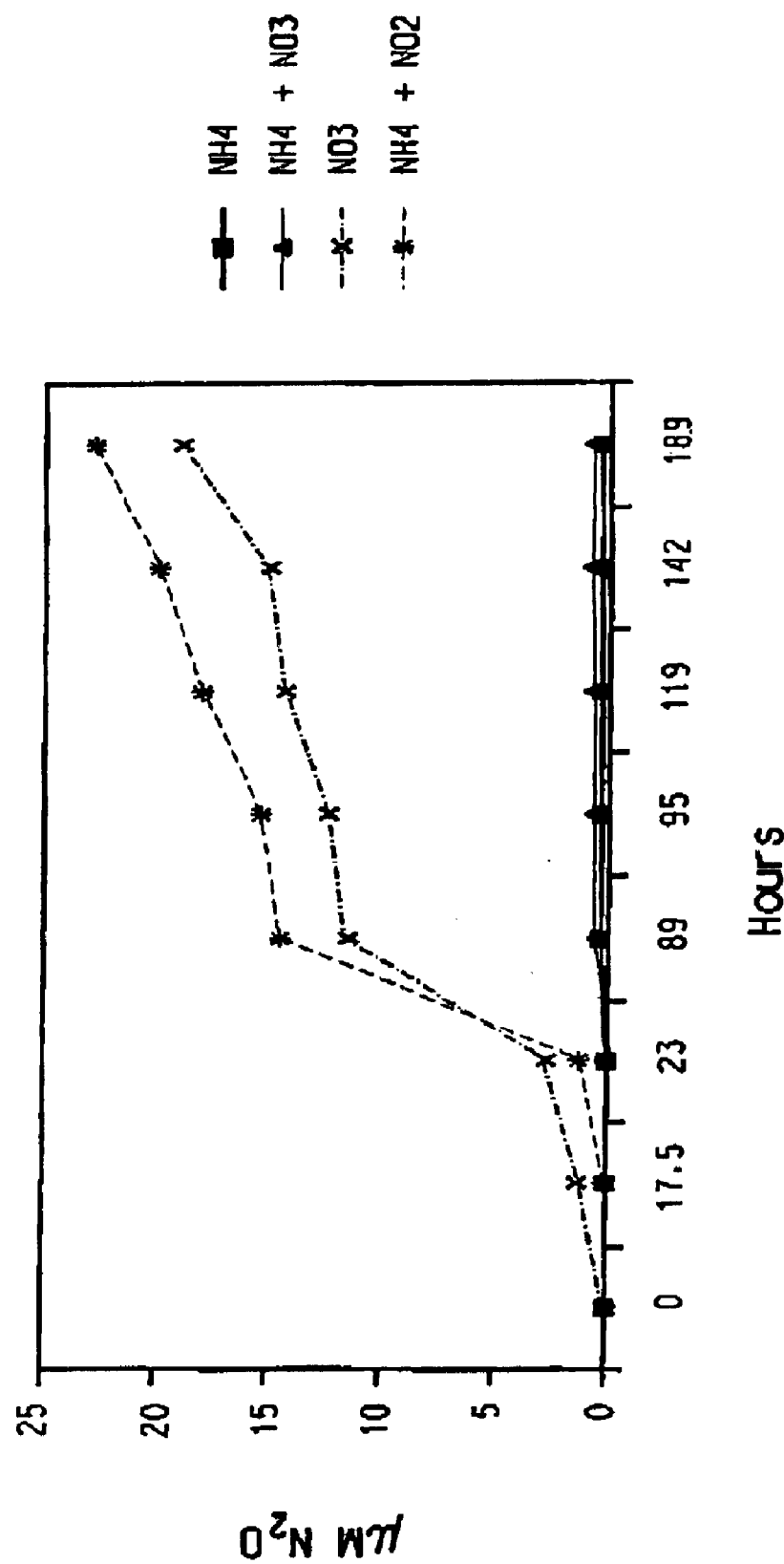

*Methylomonas* 16a cell suspensions were shown to reduce both nitrate and nitrite to nitrous oxide as shown in FIG. 1. *Methylomonas* 16a was pregrown in a simple salts solution (BTZ-NaNO$_3$, see medium formulation below) with nitrate as the sole source of nitrogen for cell growth.

| | (Per 1 L final volume) |
|---|---|
| BTZ-NaNO$_3$ | |
| NaNO$_3$ | 0.85 g |
| KH$_2$PO$_4$ | 0.5 g |
| MgCl$_2$.6H$_2$O | 0.2 g |
| CaCl.2H$_2$O | 0.1 g |
| 1 M HEPES buffer pH-7 | 50 mL |
| Solution 1 | 10 mL |
| Na$_2$SO$_4$ | 0.5 g |
| SOLUTION 1 | |
| Nitrilotriacetic Acid | 12.8 g |
| FeCl$_2$.4H$_2$O | 0.3 g |
| CuCl$_2$.2H$_2$O | 0.0254 g |
| MnCl$_2$.4H$_2$O | 0.1 g |
| CoCl$_2$.6H$_2$O | 0.312 g |
| ZnCl$_2$ | 0.1 g |
| H$_3$BO$_3$ | 0.01 g |
| Na$_2$MoO$_4$.2H$_2$O | 0.01 g |
| NiCl$_2$.6H$_2$O | 0.184 g |
| Mix, Adjust pH to 7 with 1 M NaOH | |
| Final volume: | 1 L. |

Cell suspensions were harvested from the growth cultures by centrifugation and re-suspended in growth medium. The cell suspensions were placed in serum-stoppered bottles (60 mL volume) under either methane (25% in air) or (methanol (100 mM)) and the following nitrogen sources were added to demonstrate conversion of nitrate (10 mM), nitrite (1 mM) or ammonium (80 mM) to nitrous oxide:

Nitrogen sources: Nitrate alone

Ammonia alone

Nitrate+ammonium

Nitrite+ammonium

The data of Example 4 show that with either methane or methanol nitrate was converted to nitrous oxide in the absence of ammonia. Ammonium ion repressed the reaction as would be expected if the reaction sequence proceeded through the assimilatory nitrate reductase (nas gene) to nitrite. Nitrite was reduced in the presence of ammonium and no repression of this reaction was noted. The data also show that although the genetic potential for transformation of ammonium ion to gaseous nitrous oxide is present in *Methylomonas* 16a, the cells did not produce this gas from ammonium ion.

What is claimed is:

1. An isolated nucleic acid fragment encoding a bacterial nitrite reductase selected from the group consisting of:
   (a) an isolated nucleic acid fragment encoding the amino acid sequence as set forth in SEQ ID NO:2,
   (b) an isolated nucleic acid fragment that hybridizes with SEQ ID NO:1 under the following hybridization conditions: (0.1 X SSC, 0.1% SDS, 65° C. and washed with 2 X SSC, 0.1% SDS, 65° C. followed by 0.1 X SSC, 0.1% SDS, 65° C.); or
   an isolated nucleic acid fragment that is complementary to (a), or (b).

2. The isolated nucleic acid fragment of claim 1 as set forth in SEQ ID NO:1.

3. An isolated polynucleotide comprising the isolated nucleic acid fragment of claim 1 operably linked to suitable regulatory sequences.

4. A transformed host cell comprising the isolated polynucleotide of claim 3.

5. The transformed host cell of claim 4 wherein the host cell is selected from the group consisting of bacteria, yeast, and filamentous fungi.

6. The transformed host cell of claim 5 wherein the host cell is selected from the group consisting of *Aspergillus, Trichoderma, Saccharomyces, Pichia, Candida, Hansenula, Salmonella, Bacillus, Acinetobacter, Rhodococcus, Streptomyces, Escherichia, Pseudomonas, Methylomonas, Methylobacter, Methylococcus, Methylosinus, Methylomicrobium, Methylocystis, Alcaligenes, Synechocystis, Anabaena, Thiobacillus, Methanobacterium, Klebsiella, Paracoccus, Rhodobacter,* and *Thiosphaera.*

* * * * *